US010238805B2

(12) United States Patent
Carmel et al.

(10) Patent No.: US 10,238,805 B2
(45) Date of Patent: Mar. 26, 2019

(54) AUTOMATIC INJECTION DEVICE FOR ADMINISTRATION OF HIGH VISCOSITY MEDICATION

(71) Applicant: ELCAM MEDICAL AGRICULTURAL COOPERATIVE ASSOCIATION LTD., Merom HaGalil (IL)

(72) Inventors: Ehoud Carmel, Yehud-Monosson (IL); Lior Raday, Ashkelon (IL)

(73) Assignee: ELCAM MEDICAL AGRICULTURAL COOPERATIVE, Bar-Am (IL)

( * ) Notice: Subject to any disclaimer, the term of this patent is extended or adjusted under 35 U.S.C. 154(b) by 69 days.

(21) Appl. No.: 14/786,696

(22) PCT Filed: Apr. 23, 2014

(86) PCT No.: PCT/IL2014/050375
§ 371 (c)(1),
(2) Date: Oct. 23, 2015

(87) PCT Pub. No.: WO2014/174519
PCT Pub. Date: Oct. 30, 2014

(65) Prior Publication Data
US 2016/0074584 A1 Mar. 17, 2016

Related U.S. Application Data

(60) Provisional application No. 61/815,257, filed on Apr. 23, 2013.

(51) Int. Cl.
*A61M 5/20* (2006.01)
*A61M 5/24* (2006.01)
(Continued)

(52) U.S. Cl.
CPC ............ *A61M 5/2033* (2013.01); *A61M 5/24* (2013.01); *A61M 5/28* (2013.01); *A61M 5/321* (2013.01);
(Continued)

(58) Field of Classification Search
CPC ........ A61M 5/2033; A61M 2005/2086; A61M 5/3204; A61M 5/24; A61M 5/28;
(Continued)

(56) References Cited

U.S. PATENT DOCUMENTS 3,880,163 A 4/1975 Ritterskamp
5,478,316 A * 12/1995 Bitdinger ............ A61M 5/2033
604/134

(Continued)

FOREIGN PATENT DOCUMENTS

EP 0516473 A1 12/1992
GB 759097 A 10/1956
(Continued)

OTHER PUBLICATIONS

International Search Report of PCT/IL2014/050375 dated Aug. 5, 2014.

*Primary Examiner* — Laura A Bouchelle
*Assistant Examiner* — Tasnim Mehjabin Ahmed
(74) *Attorney, Agent, or Firm* — Sughrue Mion, PLLC

(57) ABSTRACT

An automatic injection device configured for injection of a material stored in a syringe into an injection site, the syringe including a generally cylindrical storage container and a piston disposed therewithin, whose exact initial axial position within the container is not predetermined, wherein axial forward displacement of the piston in the container forces the material forwardly out of the container, the automatic injection device including at least one spring drive assembly operative, when actuated, to initially apply a first axial force (Continued)

to the syringe, thereby to axially displace the syringe in a forward direction, and thereafter, responsive to driving engagement with the piston, to apply a second axial force, substantially greater than the first axial force, notwithstanding the fact that the exact axial position of the piston within the container is not predetermined, to the piston, thereby to axially forwardly displace the piston relative to the syringe.

20 Claims, 39 Drawing Sheets

(51) Int. Cl.
    *A61M 5/32*     (2006.01)
    *A61M 5/28*     (2006.01)

(52) U.S. Cl.
    CPC ..... *A61M 5/3243* (2013.01); *A61M 2005/208* (2013.01)

(58) Field of Classification Search
    CPC ...... A61M 5/321; A61M 5/3243; A61M 5/20; A61M 5/3257; A61M 2005/3258; A61M 2005/206; A61M 2005/208; A61M 2005/2026; A61M 2005/3238
    See application file for complete search history.

(56) References Cited

U.S. PATENT DOCUMENTS

| | | | |
|---|---|---|---|
| 6,210,369 B1 | 4/2001 | Wilmot et al. | |
| 7,569,035 B1* | 8/2009 | Wilmot | A61M 5/2033 604/187 |
| 8,372,031 B2 | 2/2013 | Elmen et al. | |
| 2009/0299295 A1* | 12/2009 | Rubinstein | A61M 5/326 604/198 |
| 2010/0010454 A1* | 1/2010 | Marshall | A61M 5/2033 604/208 |
| 2011/0087163 A1 | 4/2011 | Elmen et al. | |
| 2012/0191047 A1 | 7/2012 | Raday et al. | |
| 2013/0023825 A1* | 1/2013 | Edwards | A61M 5/2033 604/143 |

FOREIGN PATENT DOCUMENTS

| | | |
|---|---|---|
| WO | 2005/070481 A1 | 8/2005 |
| WO | 2011/048422 A2 | 4/2011 |

\* cited by examiner

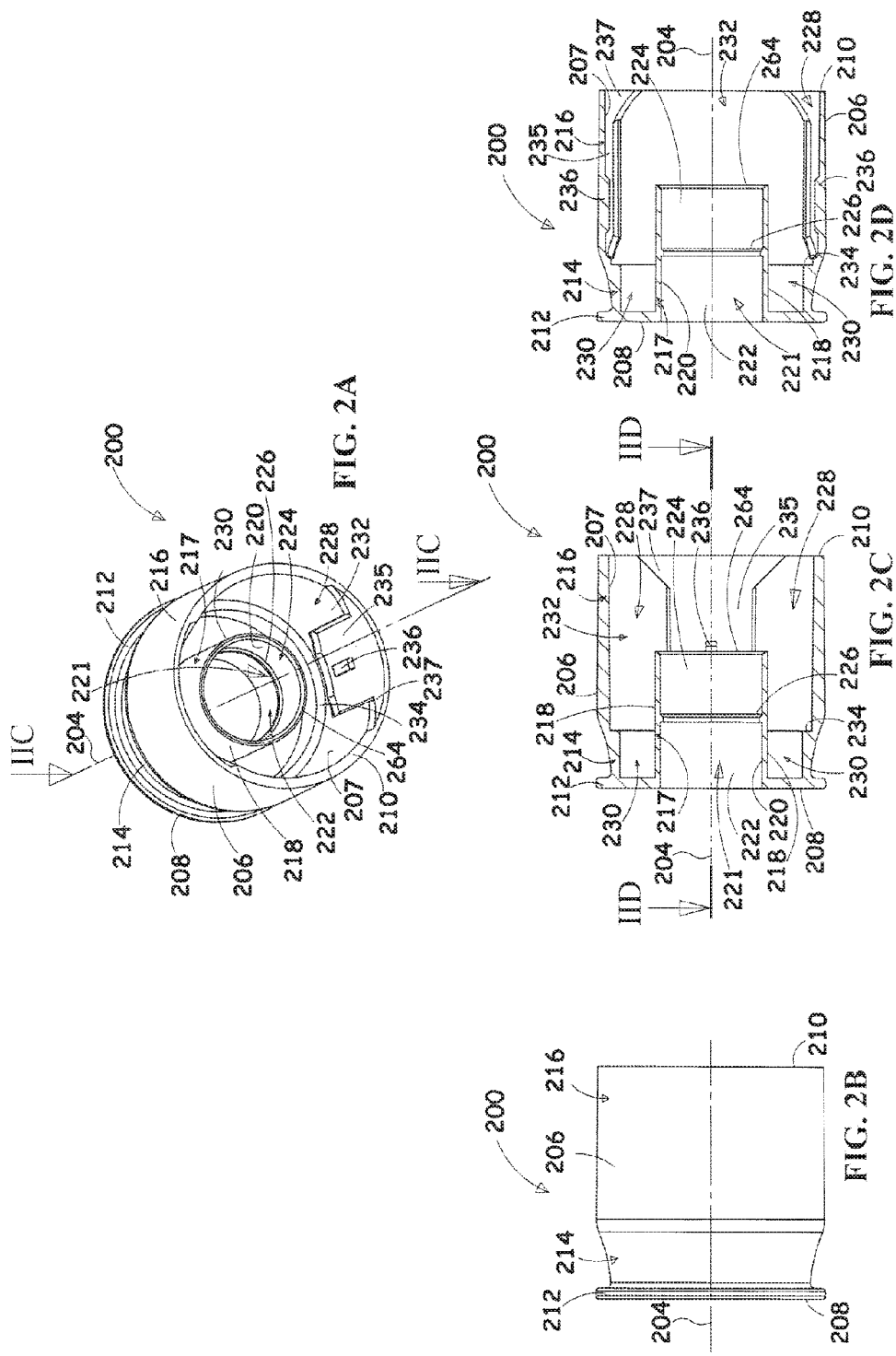

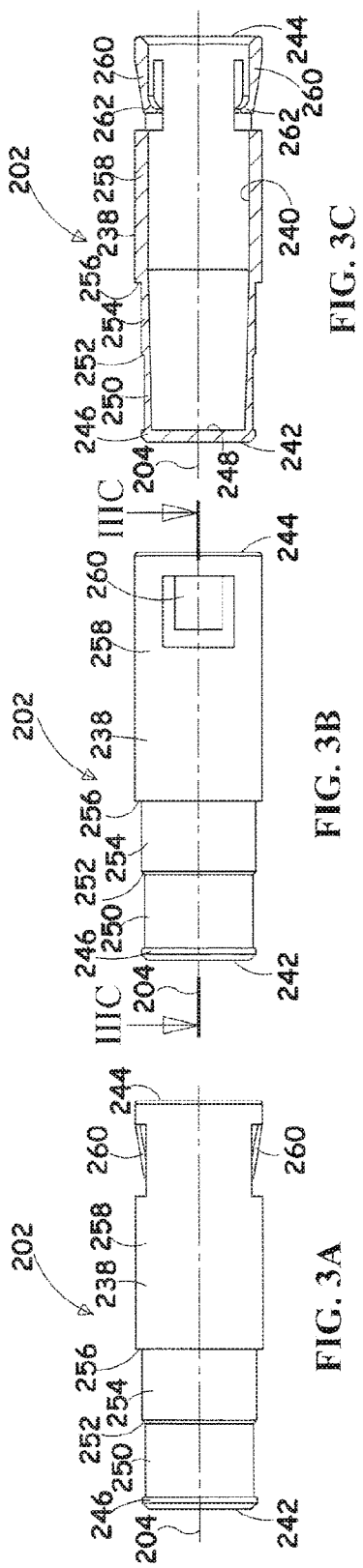

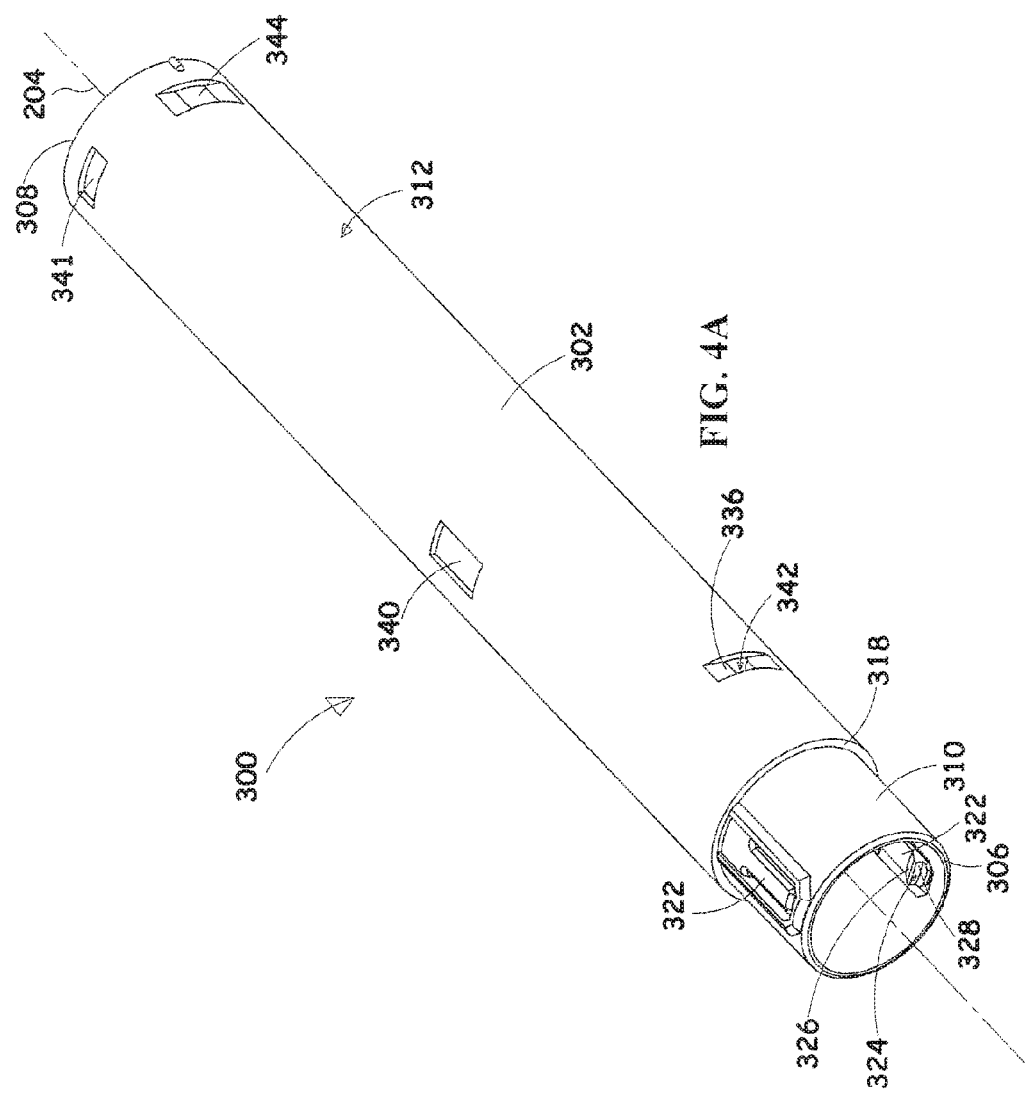

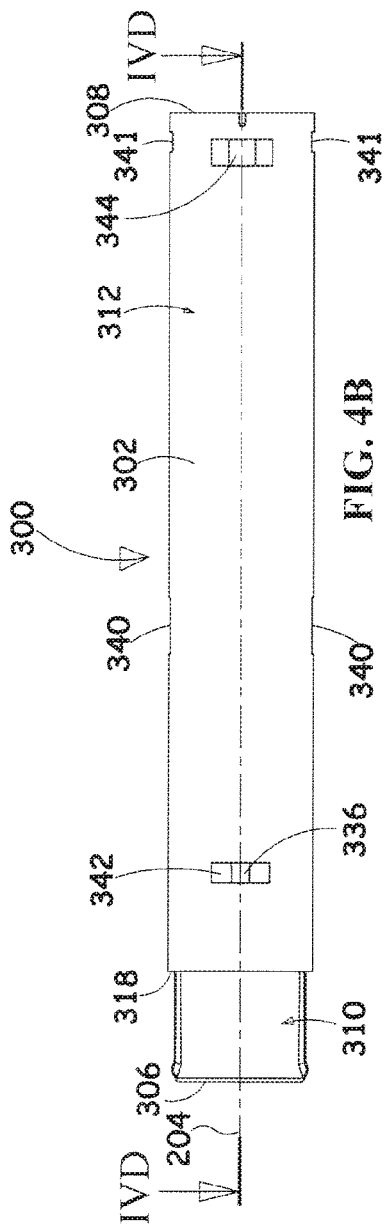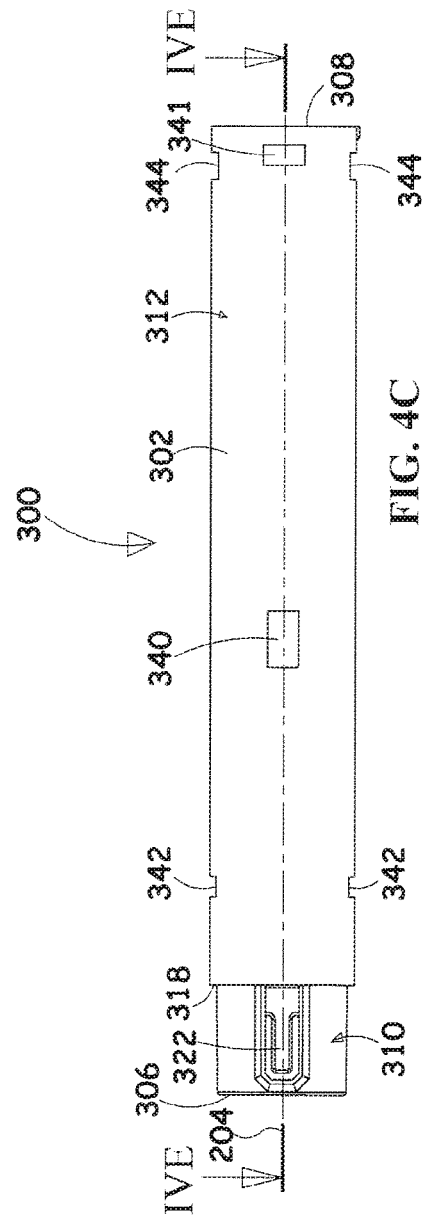

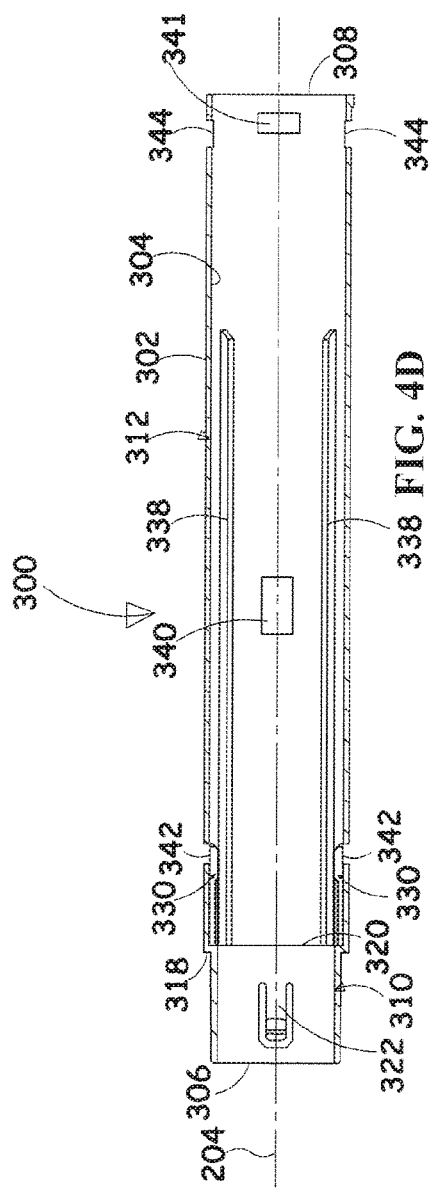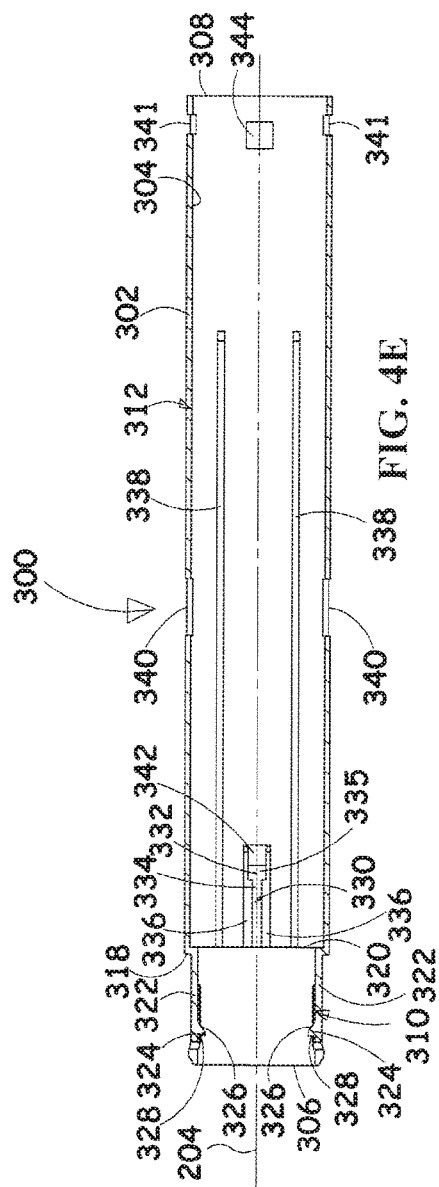

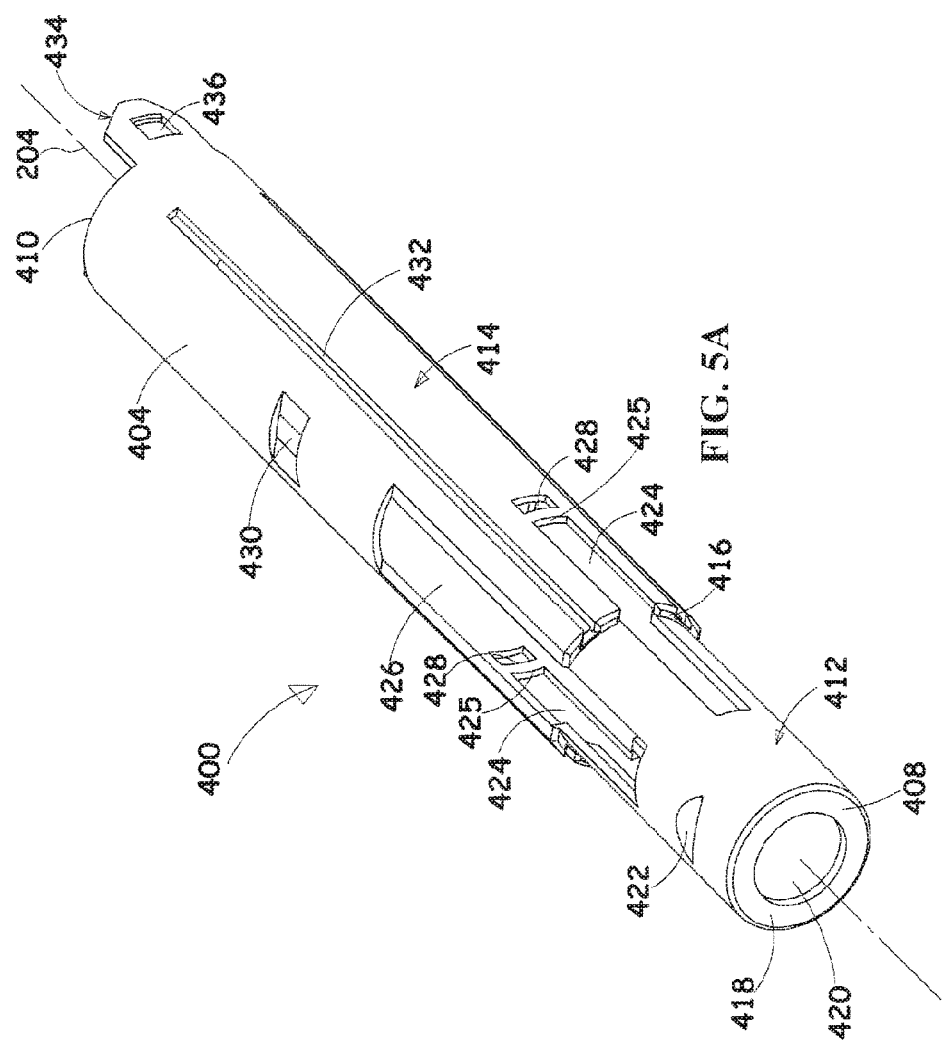

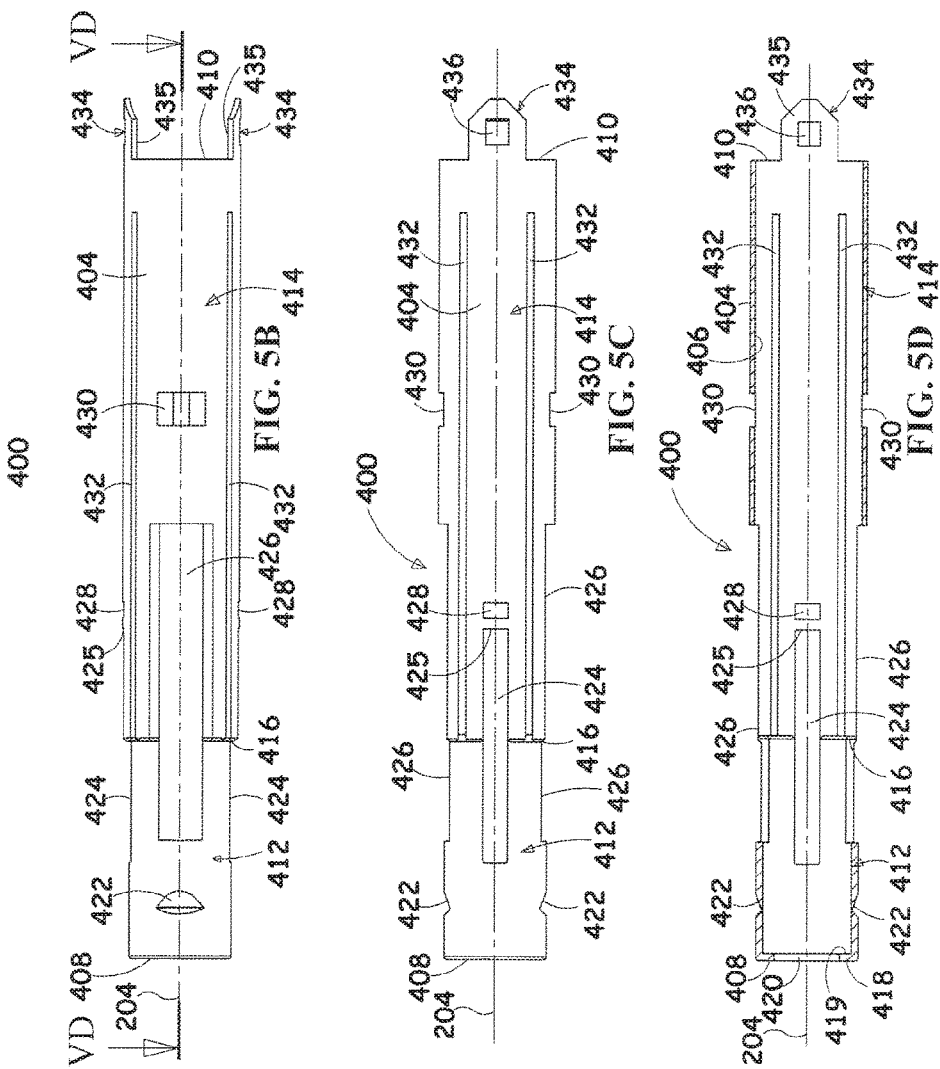

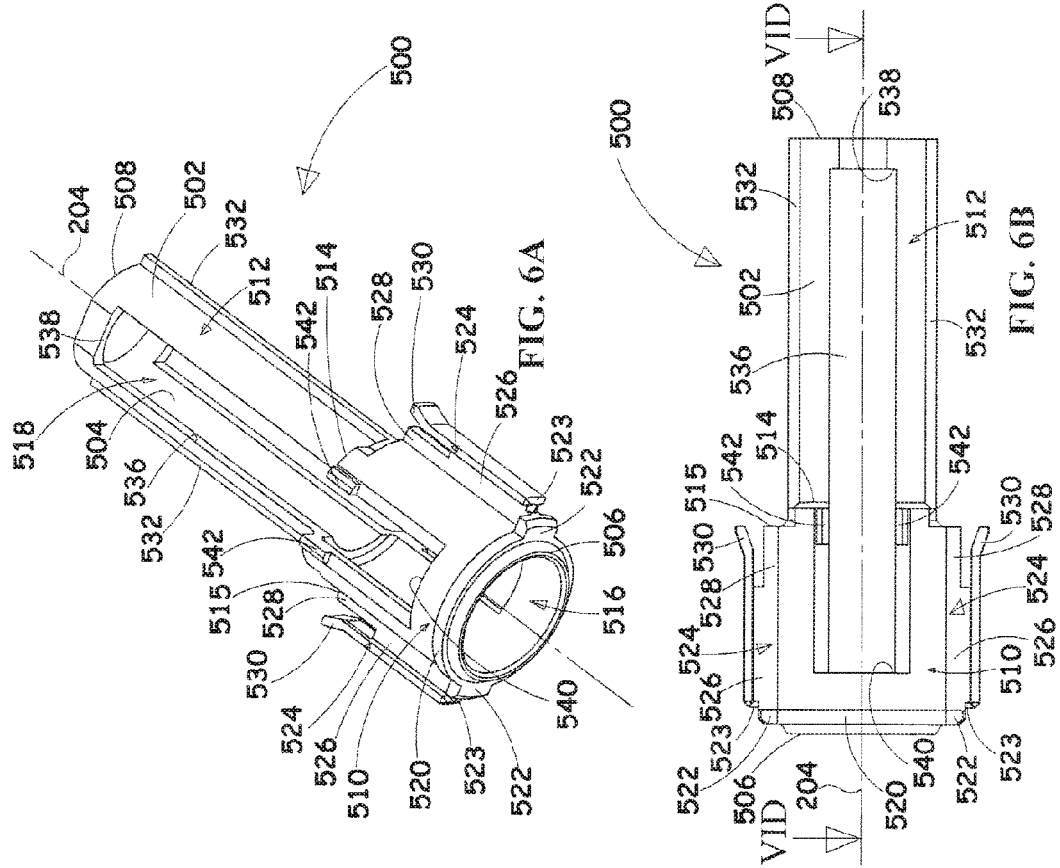

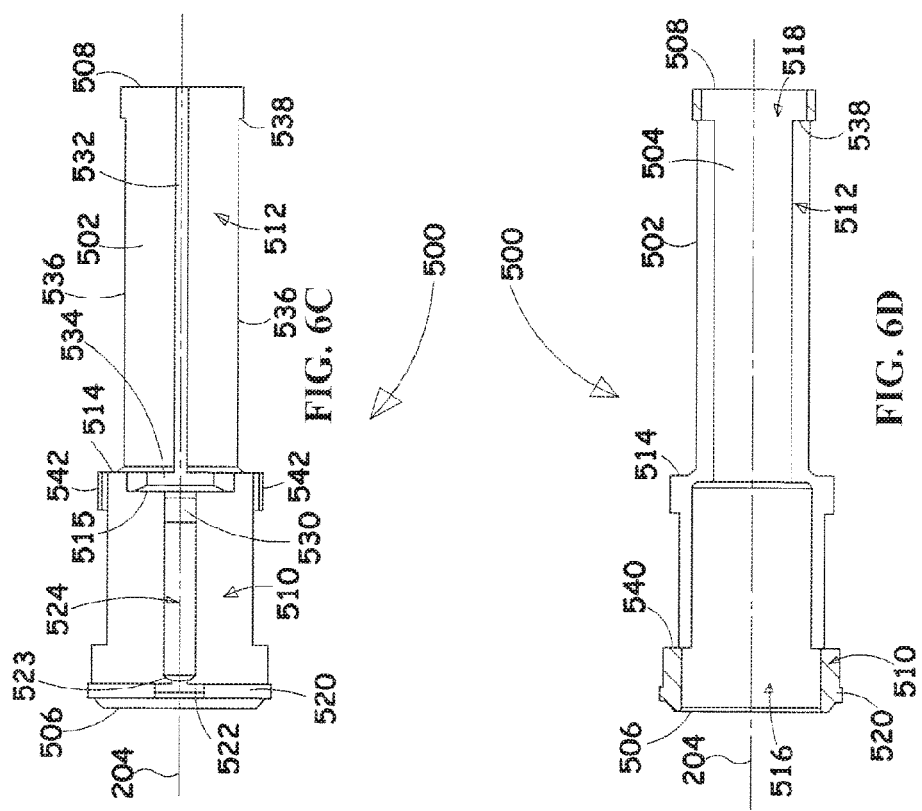

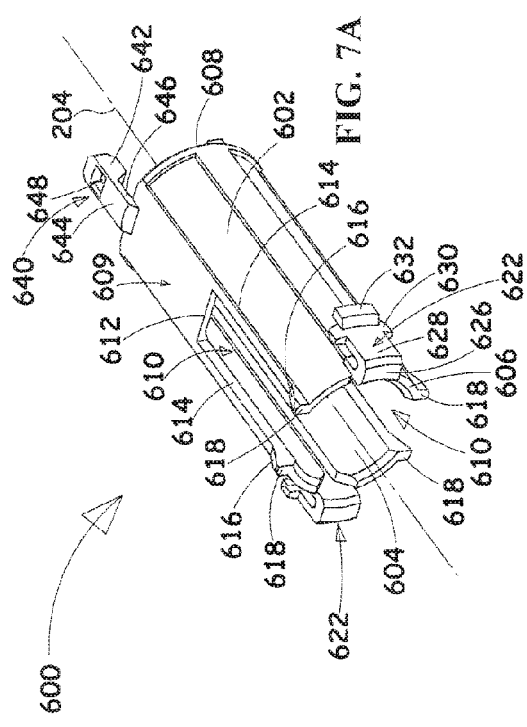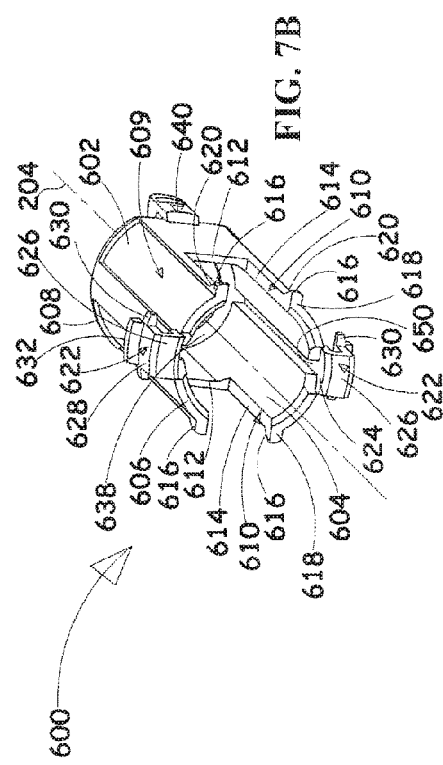

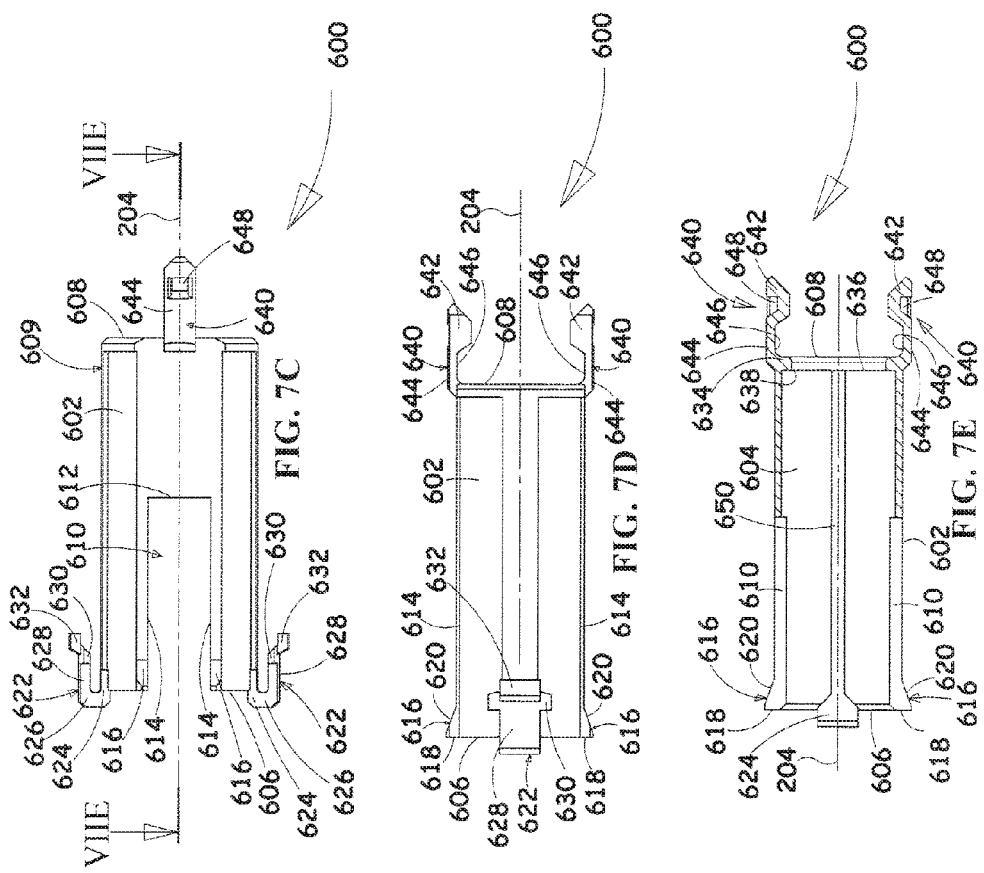

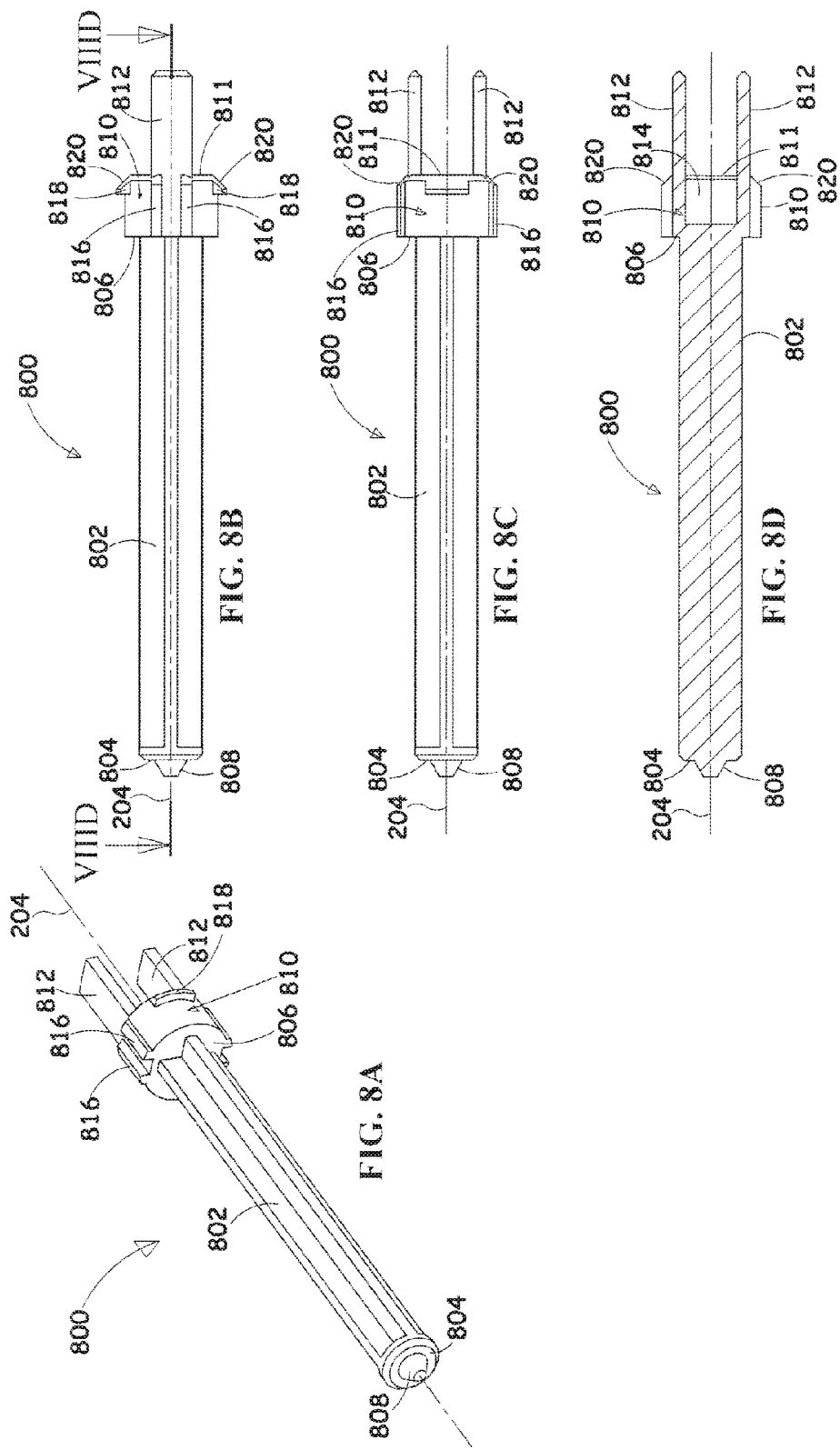

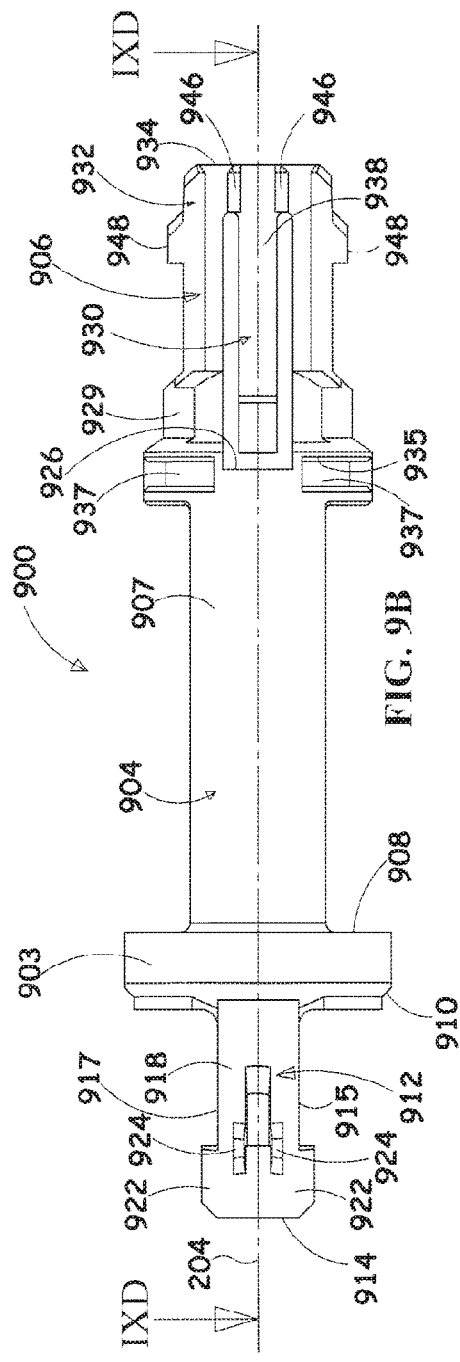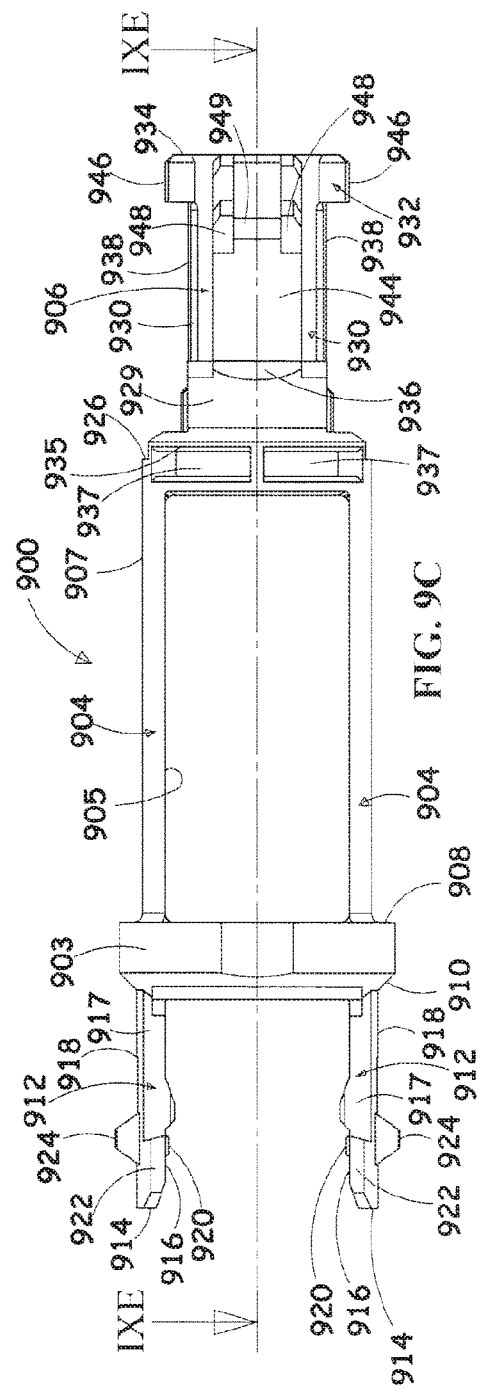

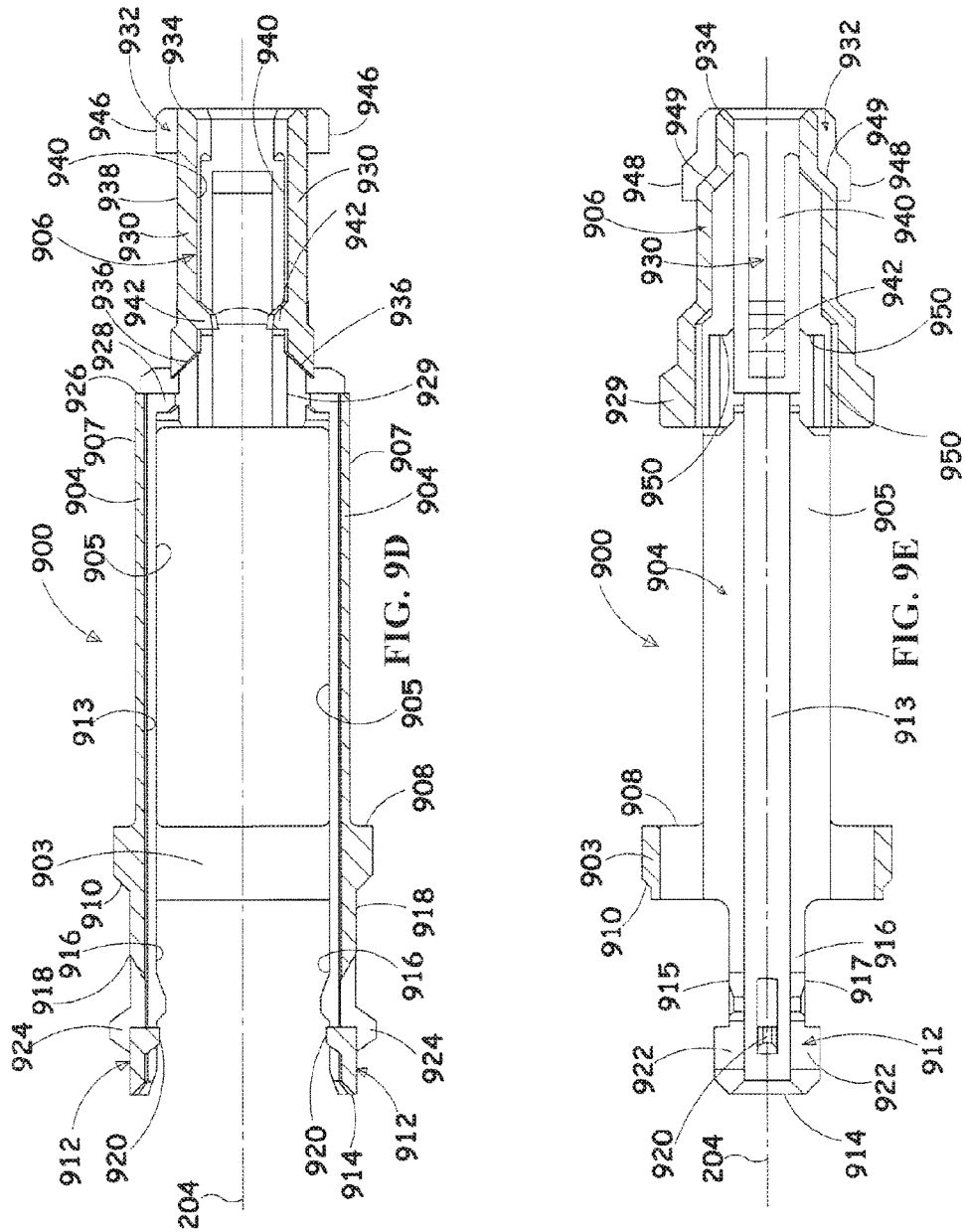

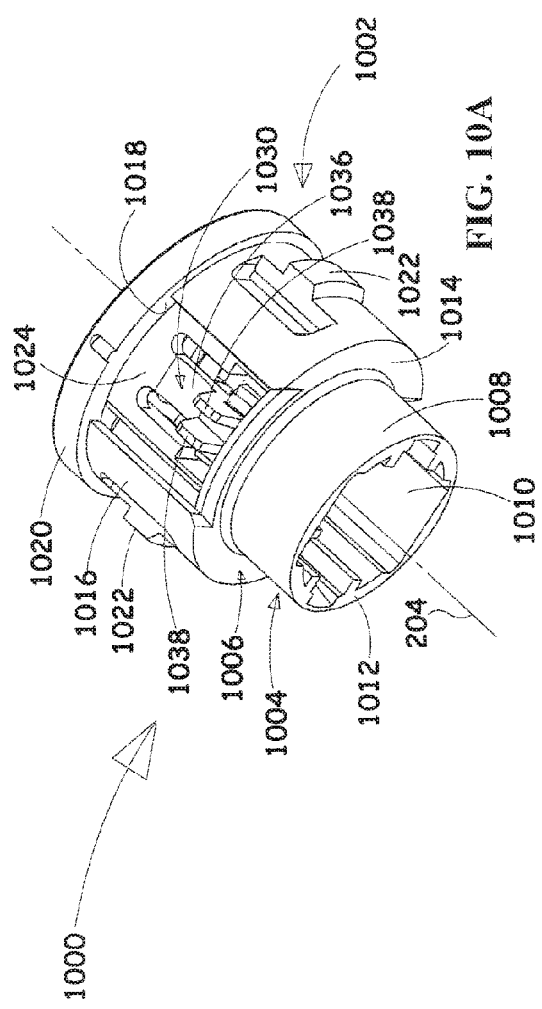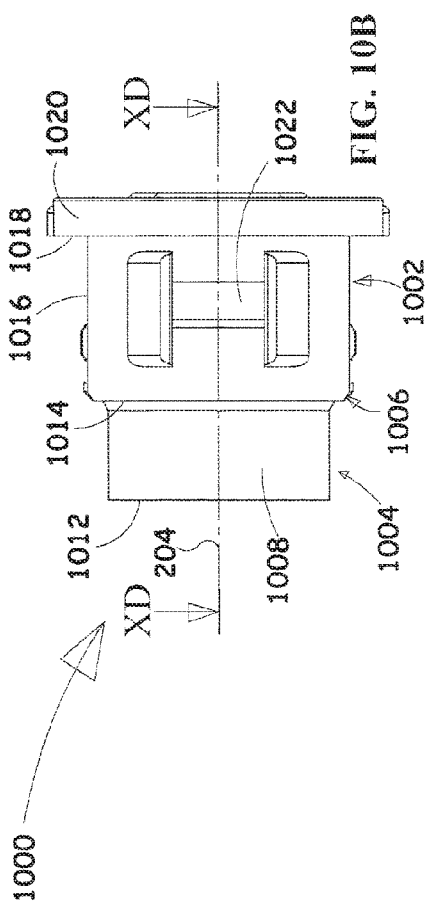

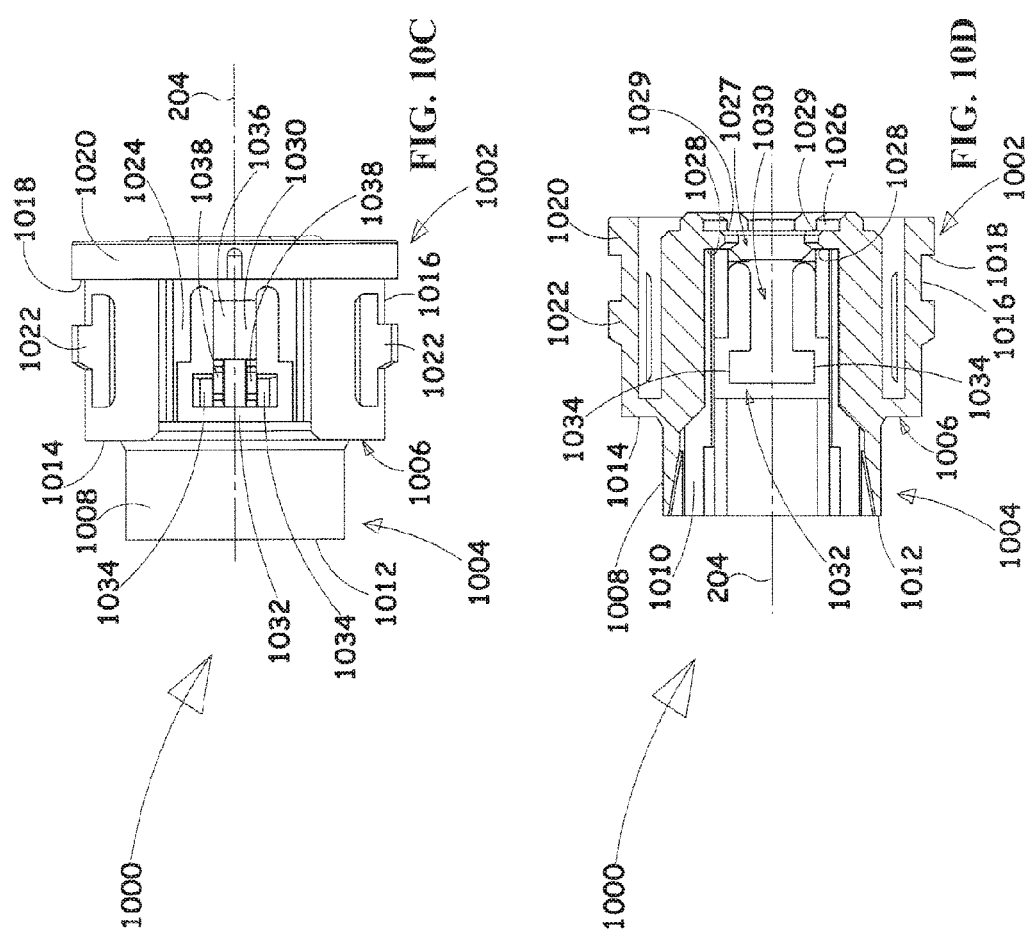

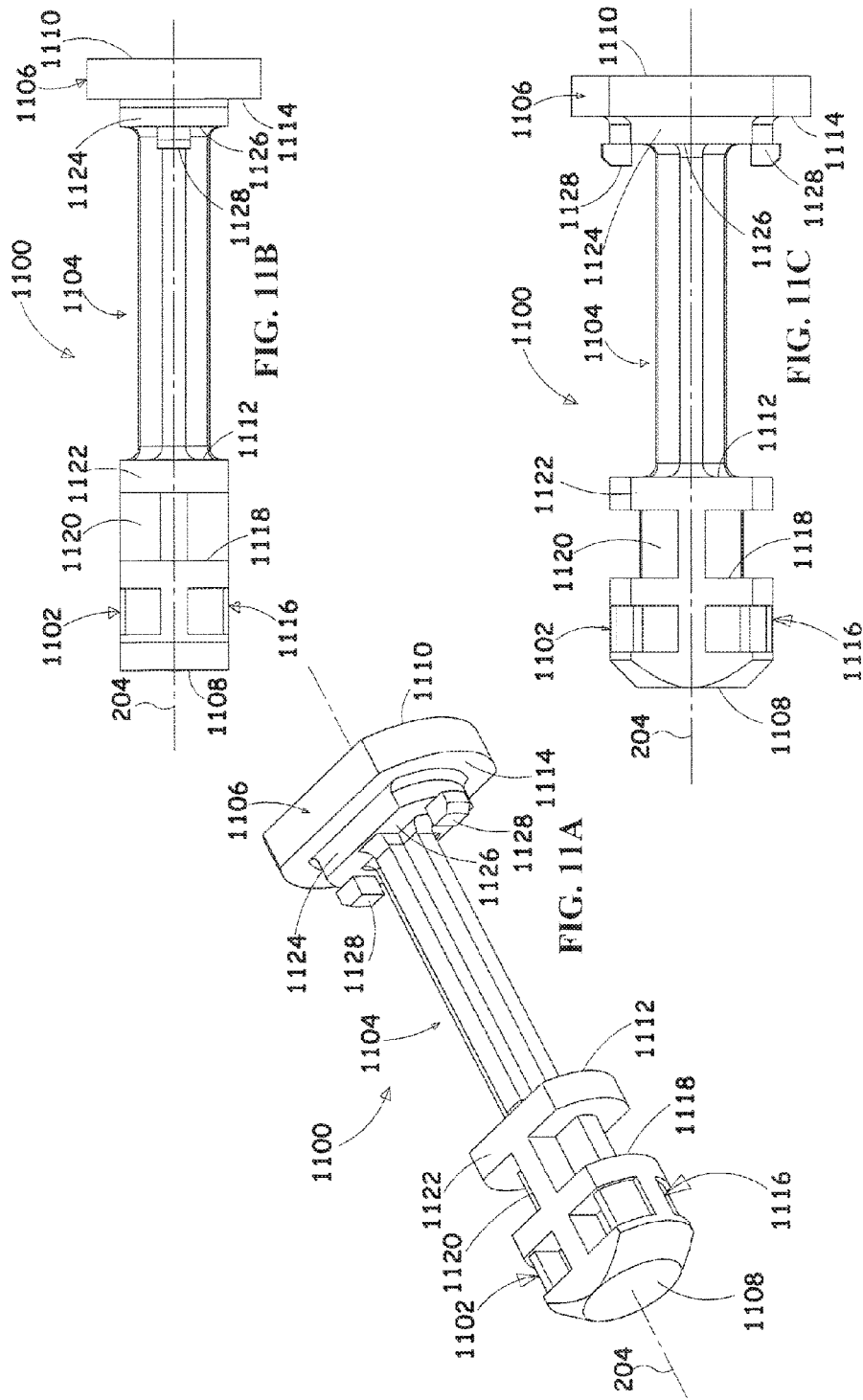

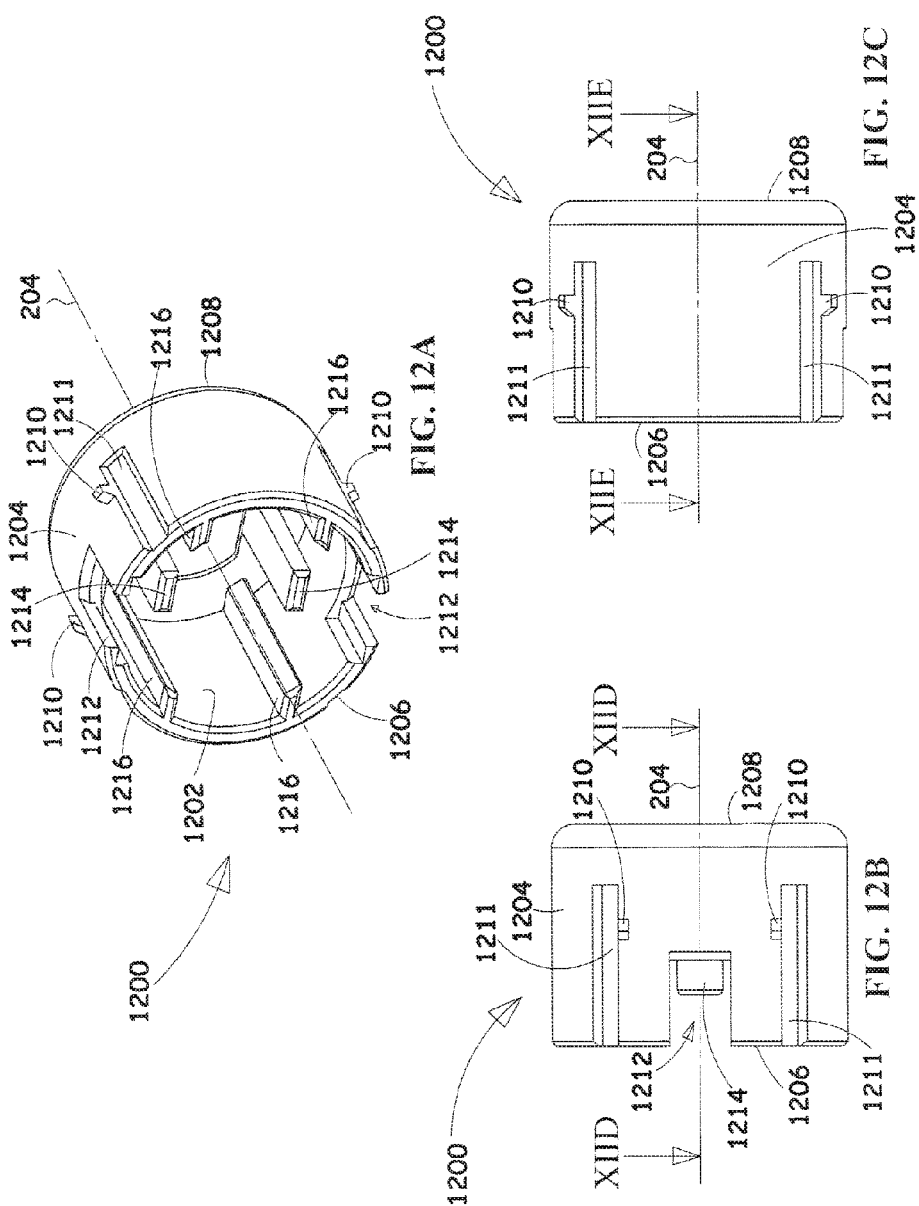

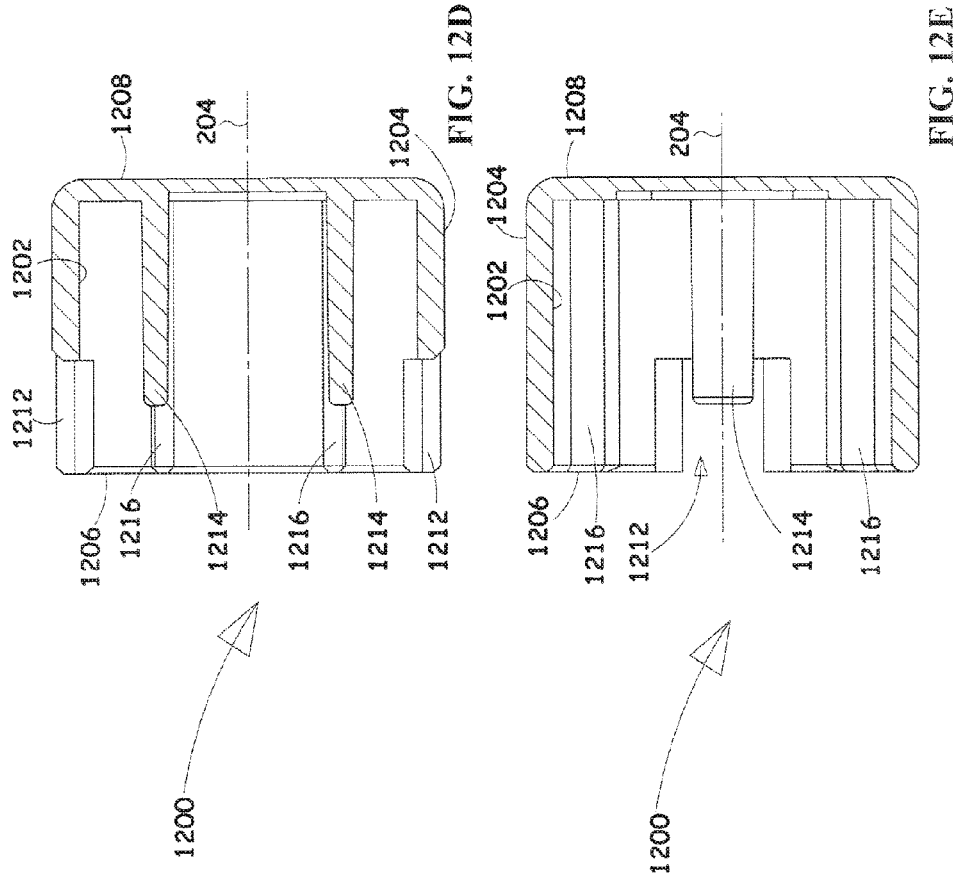

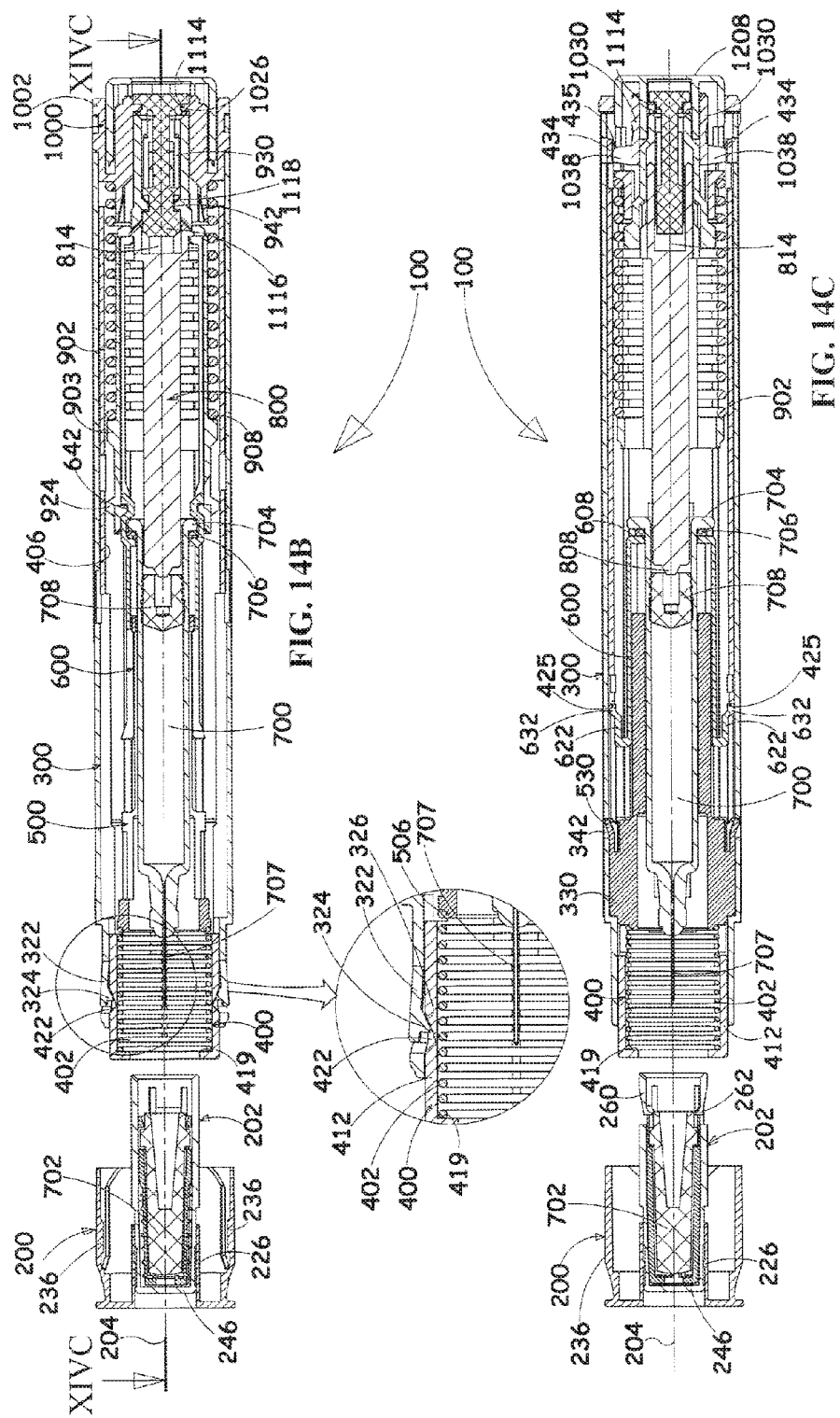

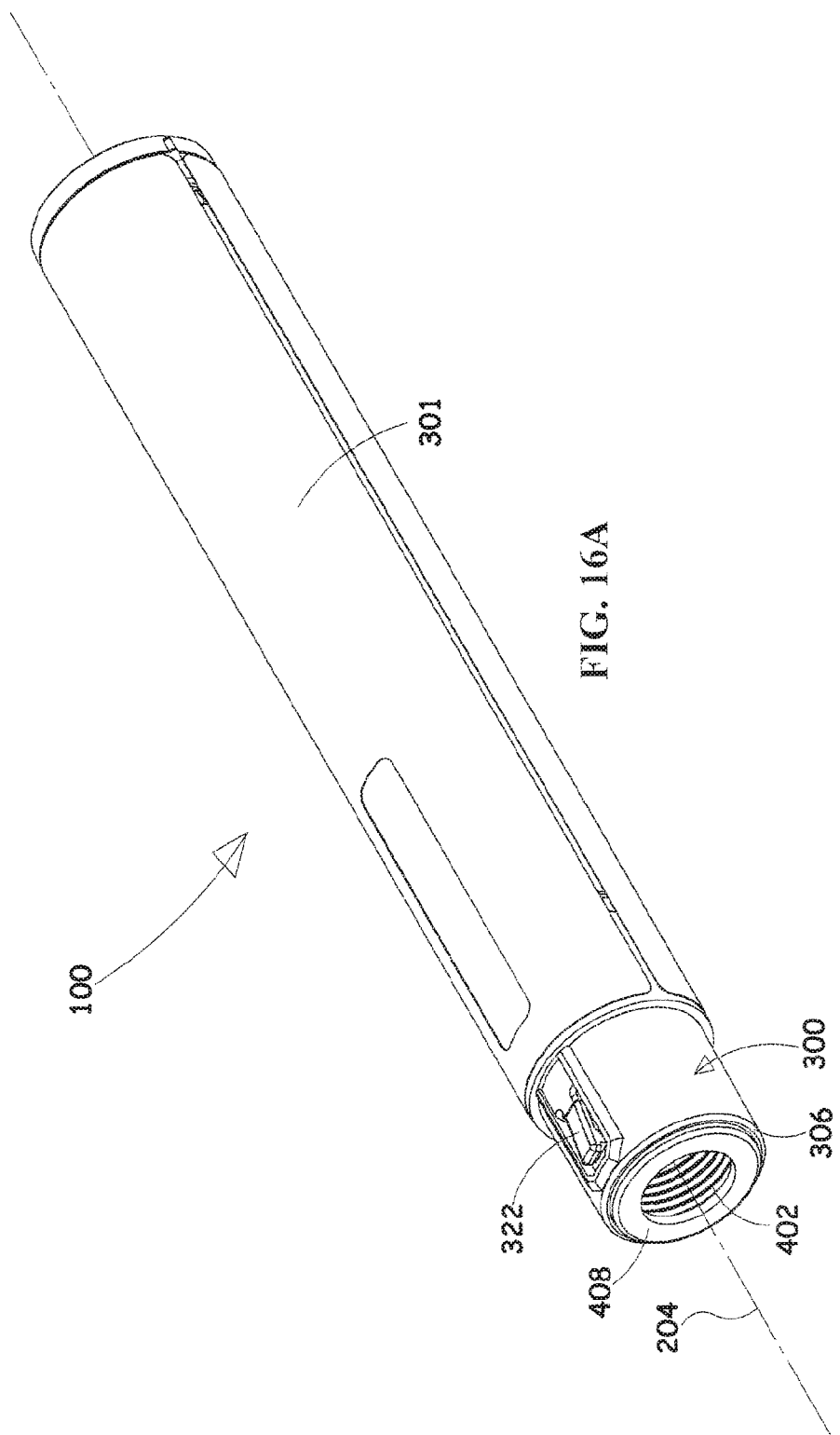

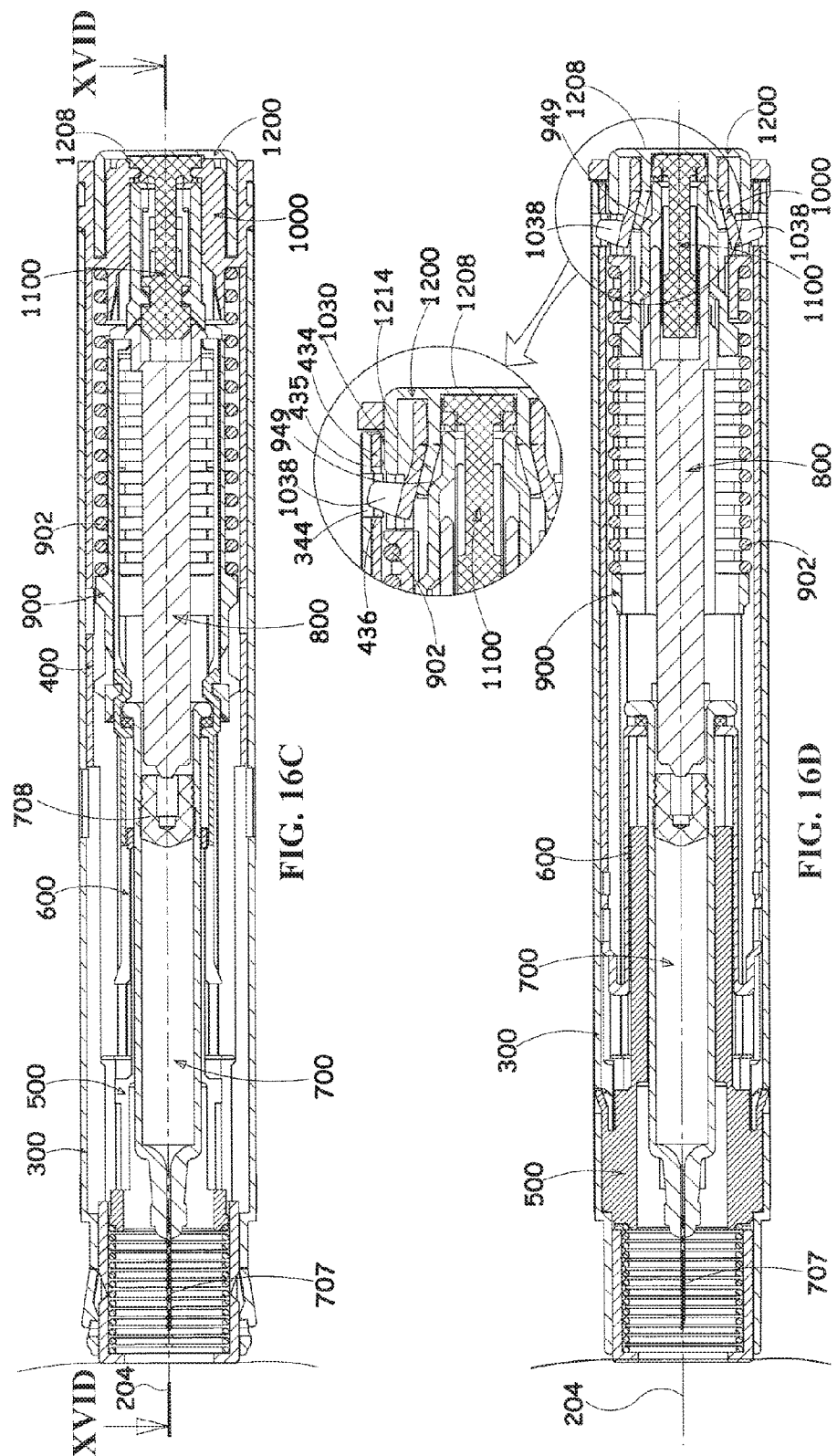

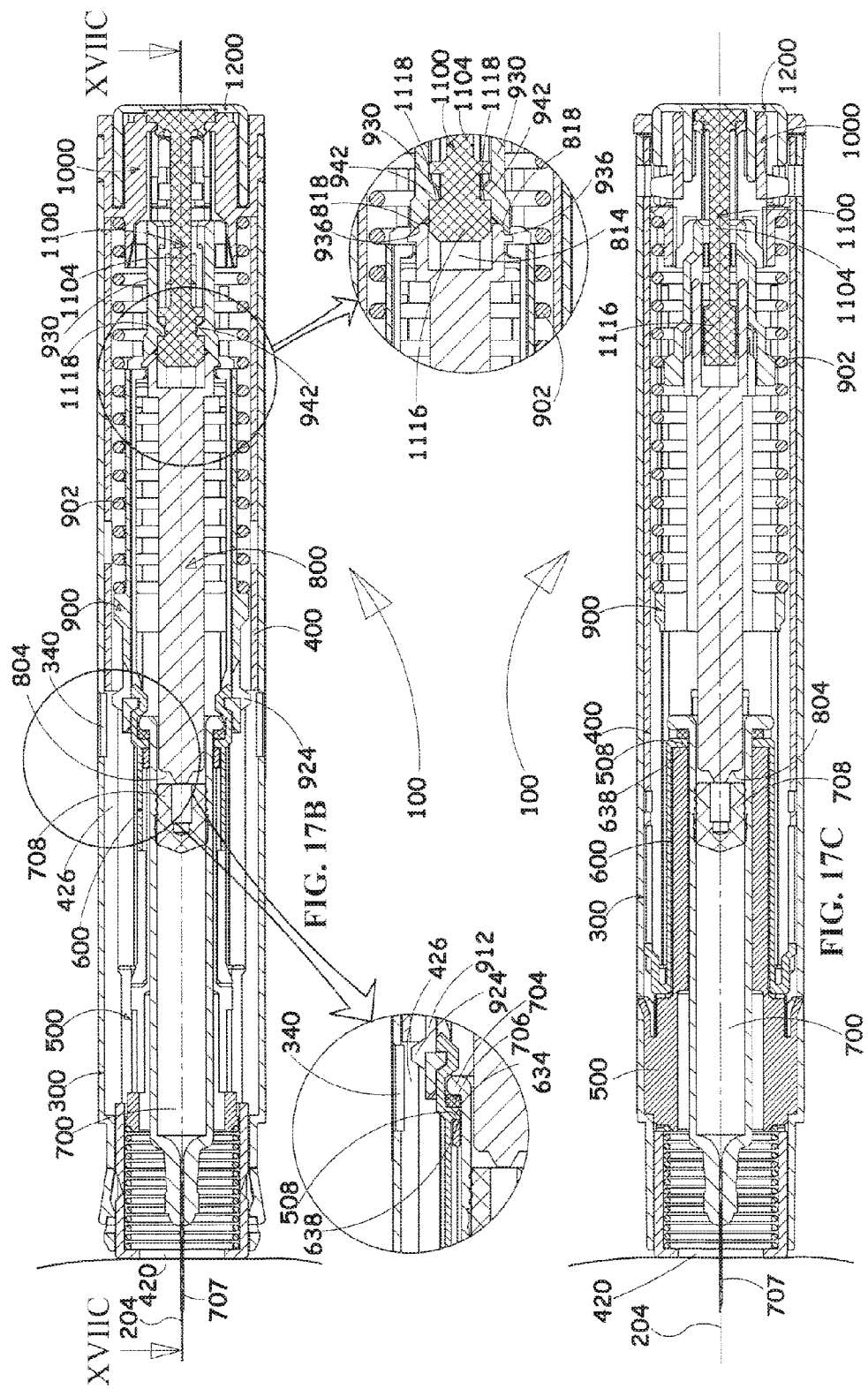

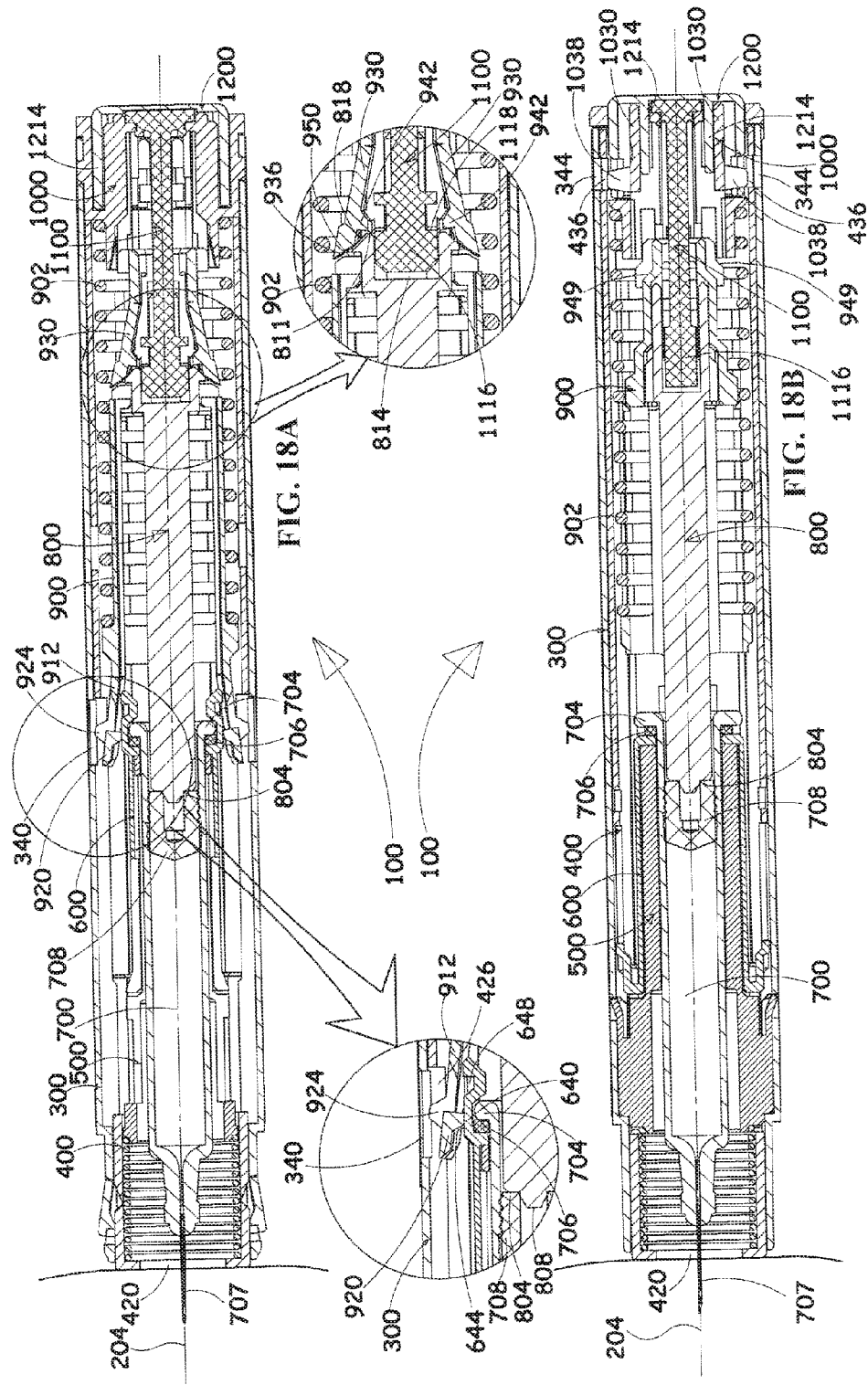

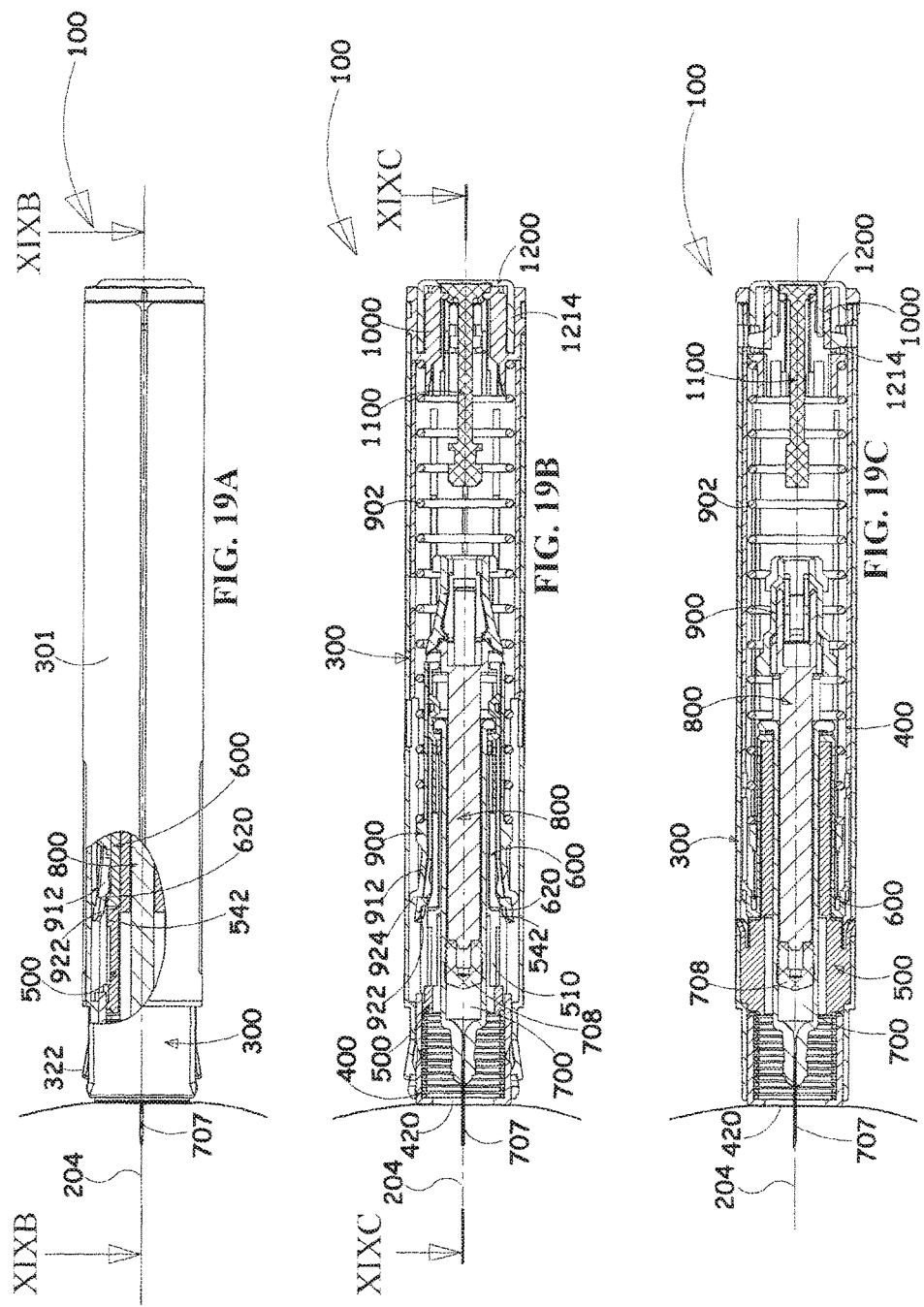

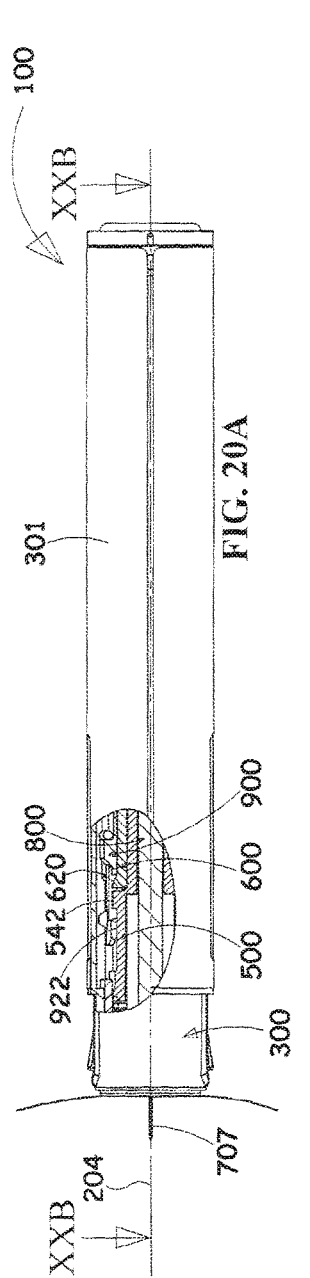
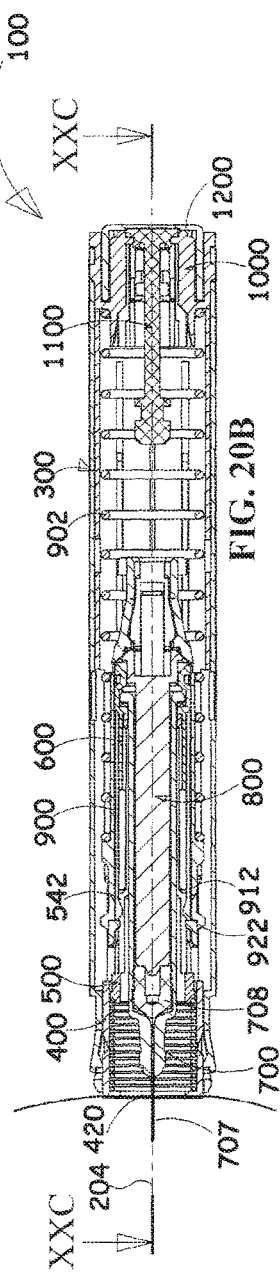
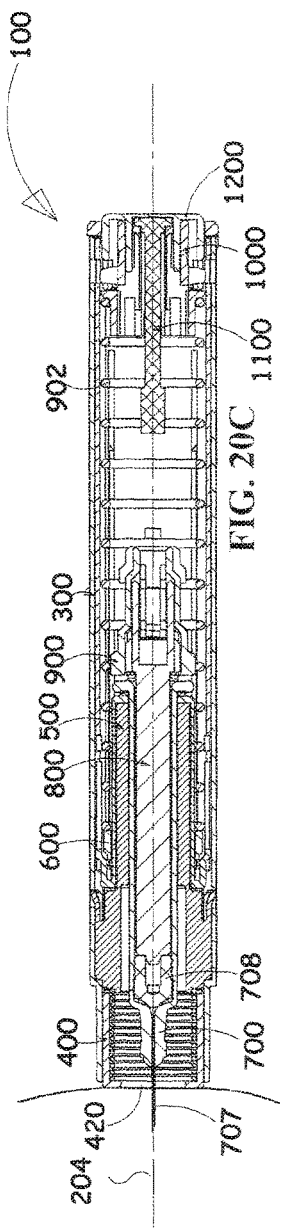
FIG. 20A
FIG. 20B
FIG. 20C

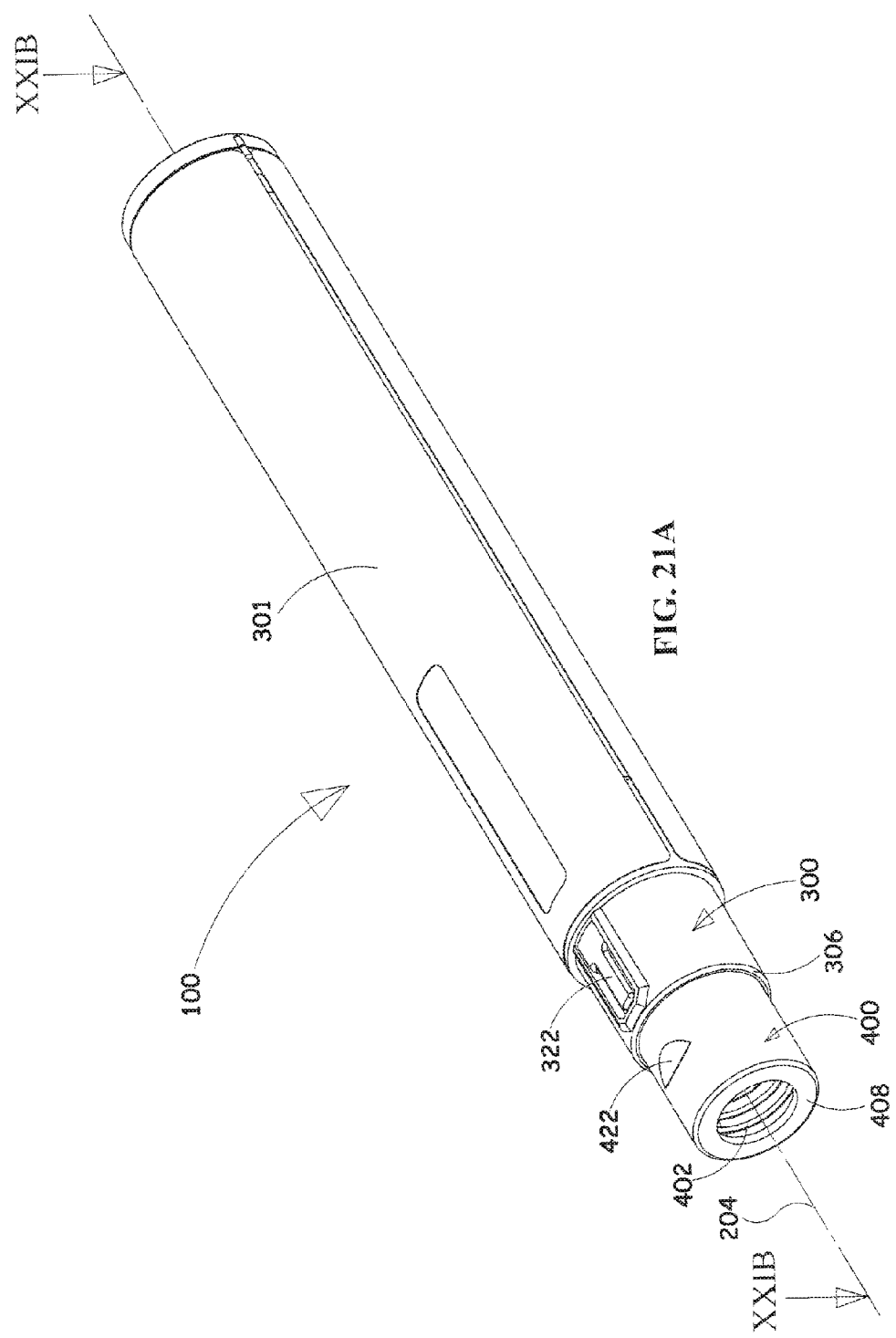

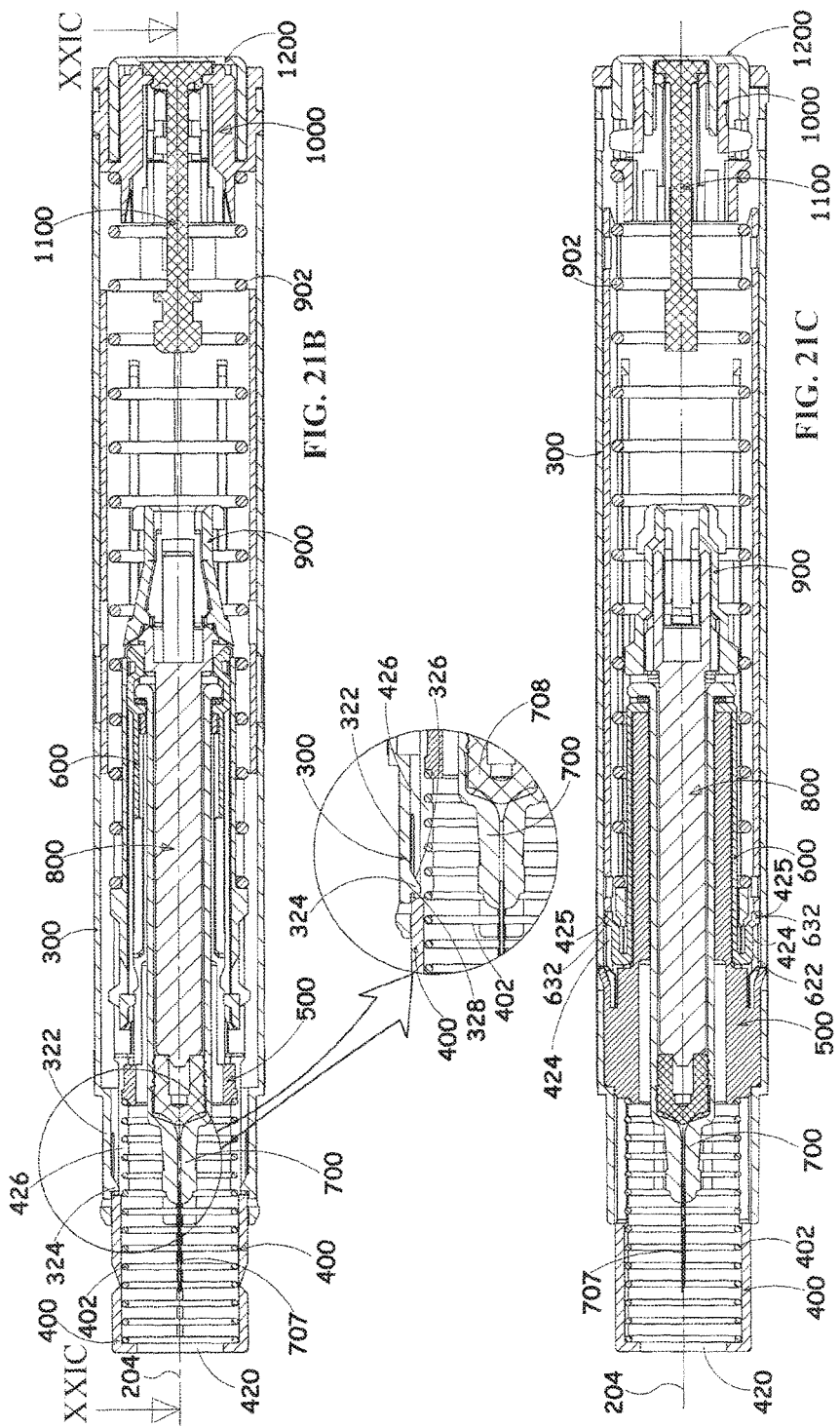

AUTOMATIC INJECTION DEVICE FOR ADMINISTRATION OF HIGH VISCOSITY MEDICATION

REFERENCE TO RELATED APPLICATIONS

This application is a National Stage of International Application No. PCT/IL2014/050375 filed Apr. 23, 2014, claiming priority based on US Provisional Patent Application No. 61/815,257, filed Apr. 23, 2013, the contents of all of which are incorporated herein by reference in their entirety.

FIELD OF THE INVENTION

The present invention relates to automatic injection devices and more particularly to automatic injection devices for administration of high viscosity medications.

BACKGROUND OF THE INVENTION

The delivery of a high viscosity medication using a syringe typically requires an automatic injector including a strong spring. One of the disadvantages in the usage of such an automatic injector having a strong spring is that it can result in the breakage of the syringe during the operation of the device. Additionally, dimensions of known automatic injection devices having strong springs are normally substantially larger than those of injectors without such springs.

SUMMARY OF THE INVENTION

The present invention seeks to provide an improved automatic injection device for high viscosity fluids.

There is thus provided in accordance with a preferred embodiment of the present invention an automatic injection device configured for injection of a material stored in a syringe into an injection site, the syringe including a generally cylindrical storage container and a piston disposed within the generally cylindrical storage container, whose exact initial axial position within the generally cylindrical storage container is not predetermined, wherein axial forward displacement of the piston in the generally cylindrical storage container forces the material forwardly out of the generally cylindrical storage container, the automatic injection device including at least one spring drive assembly operative, when actuated, to initially apply a first axial force to the syringe, thereby to axially displace the syringe in a forward direction, and thereafter, responsive to driving engagement with the piston, to apply a second axial force, substantially greater than the first axial force, notwithstanding the fact that the exact axial position of the piston within the generally cylindrical storage container is not predetermined, to the piston, thereby to axially displace the piston relative to the syringe in the forward direction.

There is also provided in accordance with another preferred embodiment of the present invention an automatic injection device configured for injection of a material stored in a syringe into an injection site, the syringe including a generally cylindrical storage container and a piston disposed within the generally cylindrical storage container, whose exact initial axial position within the generally cylindrical storage container is not predetermined, wherein axial forward displacement of the piston in the generally cylindrical storage container forces the material forwardly out of the generally cylindrical storage container, the automatic injection device including at least one spring drive assembly operative, when actuated, to initially apply a first axial force to a plunger to axially displace the plunger in a forward direction, and thereafter, responsive to engagement of the plunger with the piston, to apply a second axial force, substantially greater than the first axial force, notwithstanding the fact that the exact axial position of the piston within the generally cylindrical storage container is not predetermined, to the piston, thereby to axially displace the piston relative to the syringe in the forward direction.

The is further provided in accordance with yet another preferred embodiment of the present invention an automatic injection device configured for injection of a material stored in a syringe into an injection site, the syringe including a generally cylindrical storage container and a piston disposed within the generally cylindrical storage container, whose exact initial axial position within the generally cylindrical storage container is not predetermined, wherein axial forward displacement of the piston in the generally cylindrical storage container forces the material forwardly out of the generally cylindrical storage container, the automatic injection device including at least one spring drive assembly including at least one spring and at least one selectably operable spring energy output force limiter, the at least one selectably operable spring energy output force limiter being automatically disabled responsive to driving engagement of the at least one spring drive assembly with the piston.

Preferably, the plunger is spaced from the piston when the automatic injection device is in a storage orientation. Additionally or alternatively, the at least one spring drive assembly is configured to forwardly displace the plunger into engagement with the piston.

In accordance with a preferred embodiment of the present invention the at least one spring drive assembly includes at least one spring and at least one selectably operable spring energy output force limiter, the at least one selectably operable spring energy output force limiter being automatically disabled responsive to driving engagement of the at least one spring drive assembly with the piston, the at least one spring providing the first axial force when the at least one selectably operable spring energy output force limiter is not disabled, and providing the second axial force when the at least one selectably operable spring energy output force limiter is disabled. Additionally or alternatively, the at least one spring drive assembly stretches the at least one selectably operable spring energy output force limiter. Alternatively or additionally, the at least one selectably operable spring energy output force limiter absorbs a portion of the force of the at least one spring drive assembly.

In accordance with a preferred embodiment of the present invention the syringe includes a needle shield and the automatic injection device also includes a needle shield remover, the needle shield remover including an exterior needle shield remover and an interior needle shield remover, the exterior needle shield remover and the interior needle shield remover being configured to permit limited relative axial movement therebetween, thereby to compensate for manufacturing tolerance inaccuracies of the automatic injection device and the syringe. Additionally, the exterior needle shield remover and the interior needle shield remover are configured to the axially displaceable relative to each other at a first operative stage and not axially displaceable relative to each other at a second operative stage.

Preferably, the automatic injection device also includes a syringe sleeve and a relative movement restrictor operative to prevent relative movement of the syringe and the syringe sleeve when the automatic injection device is in a storage orientation. Preferably, the automatic injection device and the syringe sleeve are configured to allow visual examination of the contents of the syringe.

In accordance with a preferred embodiment of the present invention the automatic injection device also includes a trigger button and a trigger button locking assembly operative to prevent forward movement of the trigger button when the automatic injection device is in a storage orientation.

Preferably, the syringe also includes a needle and a needle shield configured to prevent exposure of the needle in a post-injection orientation.

In accordance with a preferred embodiment of the present invention the automatic injection device also includes a front housing, a needle shield and a trigger button, the automatic injection device being configured to be activatable by forwardly displacing the trigger button after rearwardly displacing the needle shield relative to the front housing. Additionally, the automatic injection device is configured such that forward displacement of the trigger button actuates the at least one spring drive assembly.

Preferably, the automatic injection device also includes a resilient ring positioned on the syringe.

BRIEF DESCRIPTION OF THE DRAWINGS

The present invention will be understood and appreciated more fully from the following detailed description, taken in conjunction with the drawings in which:

FIGS. 2A and 2B are simplified rear facing pictorial view and side view illustrations of an exterior Rigid Needle Shield (RNS) remover forming part of the AIDAHVM of FIG. 1;

FIGS. 2C and 2D are simplified sectional view illustrations of the exterior RNS remover as shown in FIGS. 2A and 2B, taken along lines IIC-IIC and IID-IID in FIGS. 2A and 2C, respectively;

FIGS. 3A and 3B are a simplified side view illustration and a simplified top view illustration of an interior Rigid Needle Shield (RNS) remover forming part of the AIDAHVM of FIG. 1;

FIG. 3C is a simplified sectional view illustration of the interior RNS remover as shown in FIGS. 3A and 3B, taken along lines IIIC-IIIC in FIG. 3B;

FIG. 4A is a simplified pictorial view illustration of a front housing forming part of the AIDAHVM of FIG. 1;

FIGS. 4B and 4C are a simplified side view illustration and a simplified top view illustration of the front housing as shown in FIG. 4A;

FIGS. 4D and 4E are simplified sectional view illustrations of the front housing as shown in FIGS. 4A-4C, taken along lines IVD-IVD and IVE-IVE in FIGS. 4B and 4C, respectively;

FIG. 5A is a simplified pictorial view illustration of a needle shield forming part of the AIDAHVM of FIG. 1;

FIGS. 5B and 5C are a simplified top view illustration and a simplified side view illustration of the needle shield as shown in FIG. 5A;

FIG. 5D is a simplified sectional view illustration of the needle shield as shown in FIGS. 5A-5C, taken along lines VD-VD in FIG. 5B;

FIG. 6A is a simplified pictorial view illustration of a fixed sleeve forming part of the AIDAHVM of FIG. 1;

FIGS. 6B and 6C are a simplified top view illustration and a simplified side view illustration of the fixed sleeve as shown in FIG. 6A;

FIG. 6D is a simplified sectional view illustration of the fixed sleeve as shown in FIGS. 6A-6C, taken along lines VID-VID in FIG. 6B;

FIGS. 7A and 7B are simplified pictorial view illustrations of a syringe sleeve forming part of the AIDAHVM of FIG. 1;

FIGS. 7C and 7D are a simplified top view illustration and a simplified side view illustration of the syringe sleeve as shown in FIG. 7A;

FIG. 7E is a simplified sectional view illustration of the syringe sleeve as shown in FIGS. 7A-7D, taken along lines VIIE-VIIE in FIG. 7C;

FIG. 8A is a simplified pictorial view illustration of a plunger rod forming part of the AIDAHVM of FIG. 1;

FIGS. 8B and 8C are a simplified top view illustration and a simplified side view illustration of the plunger rod as shown in FIG. 8A;

FIG. 8D is a simplified sectional view illustration of the plunger rod as shown in FIGS. 8A-8C, taken along lines VIIID-VIIID in FIG. 8B;

FIGS. 9B and 9C are a simplified side view illustration and a simplified top view illustration of the control unit as shown in FIG. 9A;

FIGS. 9D and 9E are simplified sectional view illustrations of the control unit as shown in FIGS. 9A-9C, taken along lines IXD-IXD and IXE-IXE, in FIGS. 9B and 9C, respectively;

FIG. 10A is a simplified pictorial view illustration of a rear housing forming part of the AIDAHVM of FIG. 1;

FIGS. 10B and 10C are a simplified side view illustration and a simplified top view illustration of the rear housing as shown in FIG. 10A;

FIG. 10D is a simplified sectional view illustration of the rear housing as shown in FIGS. 10A-10C, taken along lines XD-XD in FIG. 10B;

FIG. 11A is a simplified pictorial view illustration of a Resilient Dampening Element (RDE) forming part of the AIDAHVM of FIG. 1;

FIGS. 11B and 11C are a simplified side view illustration and a simplified top view illustration of the RDE as shown in FIG. 11A;

FIG. 12A is a simplified pictorial view illustration of a trigger button forming part of the AIDAHVM of FIG. 1;

FIGS. 12B and 12C are a simplified top view illustration and a simplified side view illustration of the trigger button as shown in FIG. 12A;

FIGS. 12D and 12E are simplified sectional view illustrations of the trigger button as shown in FIGS. 12A-12C, taken along lines XIID-XIID and XIIE-XIIE, in FIGS. 12B and 12C, respectively;

FIGS. 14B and 14C are simplified sectional view illustrations of the AIDAHVM as shown in FIG. 14A, taken along lines XIVB-XIVB and XIVC-XIVC, in FIGS. 14A and 14B, respectively;

FIG. 16A is a simplified pictorial view illustration of the AIDAHVM of FIGS. 1-12D in a third operative orientation, which is an activation orientation;

FIGS. 16C and 16D are simplified sectional view illustrations of the AIDAHVM as shown in FIGS. 16A-16B, taken along lines XVIC-XVIC- and XVID-XVID, in FIGS. 16B and 16C, respectively;

FIGS. 17B and 17C are simplified sectional view illustrations of the AIDAHVM as shown in FIG. 17A in a needle penetration operative orientation, taken along lines XVIIB-XVIIB and XVIIC-XVIIC, in FIGS. 17A and 17B, respectively;

FIGS. 18A and 18B are simplified sectional view illustrations of the AIDAHVM as shown in FIG. 17A in a start of injection operative orientation, along the same lines as FIGS. 17B and 17C, respectively;

FIG. 19A is a simplified, partially cut away, front view illustration of the AIDAHVM as shown in FIG. 17A in an injection operative orientation;

FIGS. 19B and 19C are simplified sectional view illustrations of the AIDAHVM as shown in FIG. 19A, taken along lines XIXB-XIXB and XIXC-XIXC, in FIGS. 19A and 19B, respectively;

FIG. 20A is a simplified, partially cut away, front view illustration of the AIDAHVM as shown in FIG. 17A in an end of injection operative orientation;

FIGS. 20B and 20C are simplified sectional view illustrations of the AIDAHVM as shown in FIG. 20A, taken along lines XXB-XXB and XXC-XXC, in FIGS. 20A and 20B, respectively;

FIG. 21A is a simplified pictorial view illustration of the AIDAHVM of FIG. 1-12D in a discard orientation; and FIGS. 21B and 21C are simplified sectional view illustrations of the AIDAHVM as shown in FIG. 21A, taken along lines XXIB-XXIB and XXIC-XXIC, in FIGS. 21A and 21B, respectively.

DETAILED DESCRIPTION OF PREFERRED EMBODIMENTS

Figure 1:
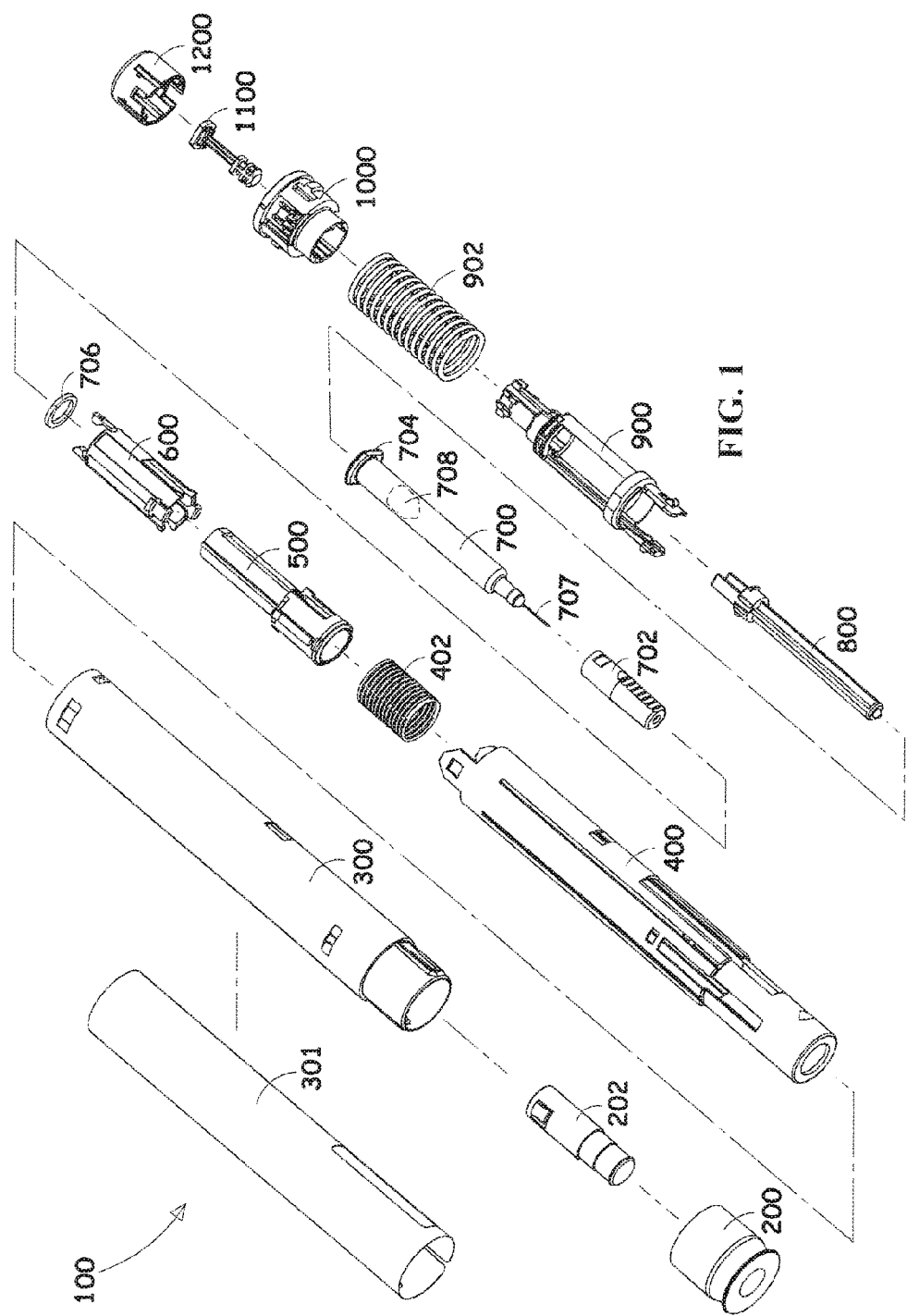
FIG. 1 is a simplified pictorial exploded view illustration of an Automatic Injection Device for Administration of High Viscosity Medication (AIDAHVM) constructive and operative in accordance with a preferred embodiment of the present invention.
Figure 13A:
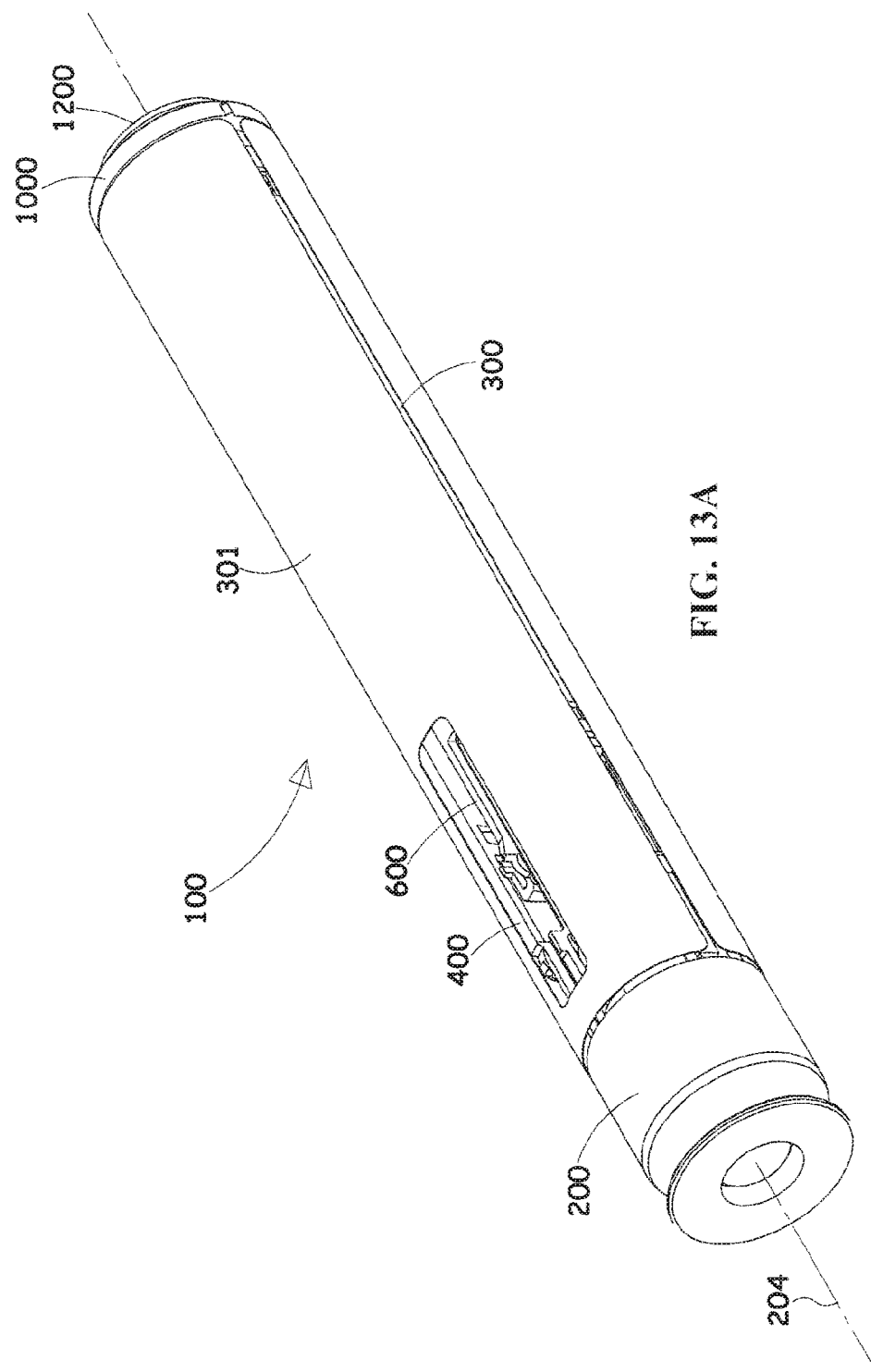
FIG. 13A is a simplified pictorial view illustration of the AIDAHVM of FIGS. 1-12D in a storage orientation.

Reference is now made to FIG. 1, which is a simplified pictorial exploded view illustration of an Automatic Injection Device for Administration of High Viscosity Medication (AIDAHVM) 100 constructive and operative in accordance with a preferred embodiment of the invention and to FIG. 13A, which is a simplified pictorial assembled view of the AIDAHVM of FIG. 1 in a storage orientation.

As seen in FIG. 1 and at least partially in FIG. 13A, AIDAHVM 100 comprises an exterior Rigid Needle Shield (RNS) remover 200 at a forward end, an interior RNS remover 202 and a front housing 300. Front housing 300 is preferably adapted to engage exterior RNS remover 200. Preferably, when AIDAHVM 100 is assembled, exterior RNS remover 200 partially surrounds interior RNS remover 202. Front housing 300 is preferably formed of a transparent material. In order to visually shield the internal mechanism of AIDAHVM 100 from a user, an opaque label 301 may cover the front housing 300.

AIDAHVM 100 also includes a needle shield 400, preferably configured to be forwardly inserted and movable relative to front housing 300. A needle shield spring 402 is adapted to be inserted within needle shield 400 to bias movement of needle shield 400 relative to front housing 300. A fixed sleeve 500 is configured to be inserted into needle shield 400 and engage needle shield spring 402. A syringe sleeve 600, positioned rearward of fixed sleeve 500, is engaged therewith and movable relative thereto.

AIDAHVM 100 also includes a syringe 700, typically a conventional syringe including a generally cylindrical storage container containing a material to be injected, typically a medication. Syringe 700 preferably includes a Rigid Needle Shield (RNS) 702, typically a conventional RNS, a needle 707, preferably adhesively attached to a forward end of syringe 700, and a piston 708, positioned within syringe 700 and generally disposed at a rearward end of syringe 700. It is appreciated that the exact initial axial position of piston 708 within syringe 700 is not predetermined. Syringe 700 defines a flange 704 at a rearward end thereof. A resilient ring 706 is preferably attached to syringe sleeve 600.

Syringe 700 is preferably operatively inserted into syringe sleeve 600. A plunger rod 800 is configured to be operatively engaged with piston 708 of syringe 700.

As seen further in FIG. 1, AIDAHVM also includes a control unit 900, operatively engaged with plunger rod 800, and at least one spring drive assembly. The at least one spring drive assembly includes an injection spring 902, which is engaged at a forward end thereof with control unit 900 and at a rearward end thereof with a rear housing 1000, and at least one selectably operable spring energy output force limiter, such as a resilient dampening element (RDE) 1100, which is configured to be located within rear housing 1000 in operative engagement with control unit 900. AIDAHVM 100 includes a trigger button 1200 at a rearmost portion thereof.

Reference is now made to FIGS. 2A and 2B, which are simplified rear facing pictorial view and side view illustrations of exterior RNS (Rigid Needle Shield) remover 200 forming part of AIDAHVM 100 of FIG. 1, and to FIGS. 2C and 2D, which are simplified sectional view illustrations of exterior RNS remover 200 as shown in FIGS. 2A and 2B.

As seen in FIGS. 2A-2D, exterior RNS remover 200 is an integrally formed element, preferably formed of plastic and arranged along a longitudinal axis 204. Exterior RNS remover 200 preferably has a generally circular cylindrical configuration, including an outer cylindrical surface 206, an inner cylindrical surface 207, a forward end 208 and a rearward end 210. Forward end 208 defines a circumferential ring 212. Outer cylindrical surface 206 of exterior RNS remover 200 includes a tapered forward portion 214 and a generally cylindrical rearward portion 216. The diameter of tapered forward portion 214 adjacent generally cylindrical rearward portion 216 is greater than the diameter thereof adjacent circumferential ring 212. A cylindrical wall portion 217 extends rearward from forward end 208 of exterior RNS remover 200. Cylindrical wall portion 217 includes an outer surface 218 and an inner surface 220 which defines a cylindrical cavity 221, including a forward cavity portion 222 and a rearward cavity portion 224 separated by an annular rearward facing flange 226. The inner diameter of annular rearward facing flange 226 is less than the diameter of rearward cavity portion 224 and is also less than the diameter of forward cavity portion 222. The diameter of rearward cavity portion 224 and the diameter of forward cavity portion 222 are typically equal. A rearward end of rearward cavity portion 224 includes an annular rearward facing flange 264.

A rearward facing shoulder 234 is formed on inner cylindrical surface 207, which divides an interior portion 228 of exterior RNS remover 200 outside of cylindrical cavity 221 into a forward annular cavity 230, extending from front end 208 to rearward facing shoulder 234, and a rearward annular portion 232, extending from rearward facing shoulder 234 to rearward end 210. The diameter of forward annular cavity 230 is less than the diameter of rearward annular portion 232.

One or more, preferably two diametrically opposite, recessed portions 235 are formed in inner cylindrical surface 207 between rearward facing shoulder 234 and rearward end 210. Recessed portion 235 is generally rectangular and includes an outwardly tapered portion 237 adjacent rearward end 210. A generally rectangular axial protrusion 236 is formed on a portion of inner cylindrical surface 207 within recessed portion 235.

Reference is now made to FIGS. 3A-3C, which are, respectively, a simplified side view illustration, a simplified top view illustration and a simplified sectional view illustration of interior RNS (Rigid Needle Shield) remover 202, forming part of AIDAHVM 100 of FIG. 1.

As seen in FIGS. 3A-3C, interior RNS remover 202 is an integrally formed element, preferably formed of plastic and arranged along longitudinal axis 204. Interior RNS remover 202 preferably has a generally cylindrical configuration, including an outer surface 238 and an inner surface 240. Interior RNS remover 202 defines a forward end 242 and a rearward end 244.

Forward end 242 of interior RNS remover 202 defines a circumferential ring 246, including a rearwardly facing inner wall 248. Outer surface 238 includes a forward portion 250 adjacent circumferential ring 246 and extending rearwardly to a first forwardly facing shoulder 252. Outer surface 238 also includes an intermediate portion 254, extending from first forwardly facing shoulder 252 to a second forwardly facing shoulder 256, and a rearward portion 258, extending from second forwardly facing shoulder 256 to rearward end 244.

The diameter of the rearward portion 258 is greater than the diameter of intermediate portion 254 and the diameter of intermediate portion 254 is greater than the diameter of forward portion 250. The diameter of circumferential ring 246 is greater than the diameter of forward portion 250.

Interior RNS remover 202 also includes one or more, preferably two diametrically opposite, connectors 260 positioned on rearward portion 258. Each connector 260 includes an inwardly radially extending arm 262, preferably a resilient radially extending arm.

Reference is now made to FIG. 4A, which is a simplified pictorial view illustration of front housing 300 forming part of AIDAHVM 100 of FIG. 1, and to FIGS. 4B-4E, which are, respectively, a simplified top view illustration, a simplified side view illustration, and first and second simplified sectional view illustrations, of front housing 300 as shown in FIG. 4A.

As seen in FIGS. 4A-4E, front housing 300 is an integrally formed element having a generally cylindrical configuration, preferably formed of plastic and arranged along longitudinal axis 204.

As described hereinabove, front housing 300 is preferably formed of a transparent material to enable a user to see, inter alia, the operative position of AIDAHVM 100. As noted hereinabove, an opaque label 301 may be provided to cover portions of front housing 300 to visually shield the internal mechanism of AIDAHVM 100 from a user. Alternatively, front housing 300 may be opaque and include a transparent window allowing visual access to at least a body of syringe 700, to enable a user to see the operative position of AIDAHVM 100.

Front housing 300 includes an outer housing surface 302, an inner housing surface 304, a forward housing end 306 and a rearward housing end 308. Front housing 300, includes a relatively short forward portion 310 and a relatively long rearward portion 312. A forwardly facing shoulder 318 is defined between relatively short forward portion 310 and relatively long rearward portion 312. The diameter of relatively long rearward portion 312 is greater than the diameter of relatively short forward portion 310.

Relatively long rearward portion 312 includes a forward end 320 adjacent forwardly facing shoulder 318.

At least one resilient arm 322 is positioned on relatively short forward portion 310. Resilient arm 322 extends radially inwardly and, as seen particularly in FIG. 4E, includes an internally extending protrusion 324, having an inwardly tapered surface 326 and a forward facing edge 328.

As seen particularly in FIG. 4E, at least one, and preferably two diametrically opposite, elongate slots 330 are formed on inner housing surface 304 of relatively long rearward portion 312 of front housing 300. Elongate slots 330 are arranged parallel to longitudinal axis 204 and extend rearwardly from forward end 320 along long rearward portion 312.

Elongate slots 330 each define an internal T-shaped recess 332, which includes a forward inner cavity portion 334 and a rearward inner cavity portion 335. The width of rearward inner cavity portion 335 is greater than the width of forward inner cavity portion 334. Extending rearwardly from forward end 320 are one or more, preferably two opposite facing, elongate elements 336 spaced from each other. Elongate elements 336 partially cover forward inner cavity portion 334.

An aperture 342 is formed in front housing 300 at a rearward end of rearward inner cavity portion 335.

One or more longitudinal ribs 338 are formed on inner housing surface 304 of relatively long rearward portion 312 of front housing 300. Longitudinal ribs 338 are arranged parallel to longitudinal axis 204 and typically extend rearwardly from forward end 320 along relatively long rearward portion 312. As seen in FIGS. 4D and 4E, longitudinal ribs 338 preferably extend only partially along the length of relatively long rearward portion to rearward housing end 308.

Relatively long rearward portion 312 of front housing 300 also preferably includes one or more, preferably two diametrically opposite, forward apertures 340 extending longitudinally and arranged parallel to axis 204. One or more, preferably two diametrically opposite, radially extending rearward apertures 341 are also formed on relatively long rearward portion 312 of front housing 300. Forward apertures 340 and rearward apertures 341 are mutually aligned along front housing 300 parallel to longitudinal axis 204. One or more rearward apertures 344 are also formed on relatively long rearward portion 312 of front housing 300 and are disposed at a radial distance of generally 90° relative to forward apertures 340 and rearward apertures 341. As seen in FIG. 4E, apertures 342 and rearward apertures 344 are preferably mutually aligned parallel to longitudinal axis 204.

Reference is now made to FIG. 5A, which is a simplified pictorial view illustration of needle shield 400 forming part of AIDAHVM 100 of FIG. 1, and to FIGS. 5B-5D, which are, respectively, a simplified top view illustration, a simplified side view illustration and a simplified sectional view illustration of needle shield 400 as shown in FIG. 5A.

As seen in FIGS. 5A-5D, needle shield 400 is an integrally formed element of a generally cylindrical shape, preferably formed of plastic and arranged along longitudinal axis 204, having an outer surface 404 and an inner surface 406, and defining a forward end 408 and a rearward end 410. Needle shield 400 preferably includes a forward portion 412 and a rearward portion 414. Preferably, the diameter of rearward portion 414 is greater than the diameter of forward portion 412. Forward portion 412 extends rearwardly from forward end 408 to a forward facing shoulder 416 and rearward portion 414 extends rearwardly from forward facing shoulder 416 to rearward end 410.

A radially extending circumferential ring 418 extends inwardly and rearwardly from forward end 408. Circumferential ring 418 defines a rearward facing edge 419 adjacent inner surface 406 of needle shield 400. An opening 420 extends rearwardly from circumferential ring 418 and is arranged parallel to longitudinal axis 204.

Needle shield 400 also includes one or more, preferably two, recessed portions 422 arranged rearwardly of rearward facing edge 419. One or more, preferably two, longitudinal openings 424 extend rearwardly from a point on forward portion 412 to rearward portion 414, each including a rearward edge 425. Needle shield 400 also includes one or more, preferably two, longitudinal indication openings 426, each extending rearwardly from a location rearward of recessed portion 422 on forward portion 412 to rearward portion 414.

Needle shield 400 further includes one or more first apertures 428, each located rearwardly of each of the one or more longitudinal openings 424. One or more second apertures 430 are also provided, each located rearwardly of each of the one or more indication openings 426.

In a most preferred embodiment, two longitudinal openings 424 are provided and are aligned with two first apertures 428. In this embodiment, longitudinal openings 424 are disposed at a radial distance of generally 90° relative to two indication openings 426, each of which are aligned with second apertures 430.

One or more longitudinal grooves 432 are formed on outer surface 404 of the rearward portion 414. Longitudinal grooves 432 extend rearwardly from forward facing shoulder 416 and typically cover most of the length of rearward portion 414.

Extending rearwardly from rearward end 410 are one or more, preferably two, tabs 434, each defining an inner surface 435 and having an aperture 436 therethrough. Tabs 434 are preferably positioned rearward of longitudinal openings 424 and at a radial distance of generally 90° relative to recessed portions 422 and indication openings 426.

Reference is now made to FIG. 6A, which is a simplified pictorial view illustration of fixed sleeve 500 forming part of AIDAHVM 100 of FIG. 1, and to FIGS. 6B-6D, which are, respectively, a simplified top view illustration, a simplified side view illustration and a simplified sectional view illustration of fixed sleeve 500 as shown in FIG. 6A.

As seen in FIGS. 6A-6D, fixed sleeve 500 is an integrally formed element having a generally cylindrical shape, preferably formed of plastic and arranged along longitudinal axis 204.

The fixed sleeve 500 includes an outer surface 502 and an inner surface 504, and defines a forward end 506 and a rearward end 508. Fixed sleeve 500 includes a forward cylindrical portion 510 and a rearward cylindrical portion 512. The diameter of forward cylindrical portion 510 is preferably greater than the diameter of rearward cylindrical portion 512. Forward cylindrical portion 510 preferably extends rearwardly from forward end 506 to a rearward facing shoulder 514 and rearward cylindrical portion 512 extends rearwardly from rearward facing shoulder 514 to rearward end 508. Forward cylindrical portion 510 defines a forward inner bore 516 and rearward cylindrical portion 512 defines a rearward inner bore 518. The diameter of forward inner bore 516 is greater than the diameter of rearward inner bore 518.

A circumferential ring 520 extends radially outwardly from forward end 506 and preferably includes one or more, preferably two diametrically opposite, radially extending protrusions 522.

Positioned rearwardly of each of radially extending protrusions 522 is a forwardly facing edge 523. A forward longitudinal rib 524 extends rearwardly from each forwardly facing edge 523 to a rearwardly facing edge 515 positioned adjacent and forwardly of rearward facing shoulder 514. Forward longitudinal ribs 524 include a top, generally planar portion, and a bottom portion, generally in the shape of a rectangular prism, including a generally wide forward portion 526 adjacent to the forwardly facing edge 523 and a generally narrow rearward portion 528 adjacent the rearward facing shoulder 514. Generally narrow rearward portion 528 of forward longitudinal rib 524 and top, generally planar, portion of forward longitudinal rib 524 define a gap therebetween. Extending outwardly from a rearward end of lop, generally planar, portion of the forward longitudinal ribs 524 is a radial extension 530.

The provision of radial extension 530 and the gap between the top, generally planar, portion of forward longitudinal rib 524 and the narrow rearward portion 528 provide for a resilient characteristic of the longitudinal ribs 524. One or more rearward longitudinal ribs 532 extend forwardly from rearward end 508 of fixed sleeve 500 to rearward facing shoulder 514. The rearward longitudinal ribs 532 are arranged parallel to longitudinal axis 204 and aligned with the forward longitudinal ribs 524.

One or more longitudinal indication openings 536 extend forwardly from an edge 538 disposed adjacent to and forwardly of the rearward end 508 of fixed sleeve 500 to an edge 540 disposed adjacent to and rearwardly of forward end 506 of fixed sleeve 500.

One or more, preferably two, protrusions 542 are disposed at opposite edges of each indication opening 536. Protrusions 542 extend radially outwardly from forward cylindrical portion 510 of fixed sleeve 500. Protrusions 542 extend forwardly from rearward facing shoulder 514 along a portion of the length of forward cylindrical portion 510 of fixed sleeve 500.

Reference is now made to FIGS. 7A and 7B, which are simplified pictorial view illustrations of syringe sleeve 600 forming part of AIDAHVM 100 of FIG. 1, and to FIGS. 7C-7E, which are, respectively, a simplified top view illustration, a simplified side view illustration and a simplified sectional view illustration of syringe sleeve 600 as shown in FIGS. 7A and 7B.

As seen in FIGS. 7A-7E, syringe sleeve 600 is an integrally formed element having a generally cylindrical shape, preferably formed of plastic and arranged along the longitudinal axis 204.

Syringe sleeve 600 includes an outer surface 602 and an inner surface 604, and defines a forward end 606 and a rearward end 608. The syringe sleeve 600 includes a cylindrical wall 609.

One or more, typically two, longitudinal openings 610 extend rearwardly, arranged parallel to longitudinal axis 204, from forward end 606 partially through the length of cylindrical wall 609. Each longitudinal opening 610 defines a rearward edge 612 and two opposed lateral edges 614.

One or more, preferably two, angular protrusions 616 are disposed on opposed lateral edges 614 of longitudinal opening 610. Angular protrusions 616 include a straight edge 618, parallel to and radially extending outwardly from forward end 606 and an inclined edge 620. between the outward end of straight edge 618 and cylindrical wall 609.

Syringe sleeve 600 also includes one or more, typically two, forward resilient arms 622, preferably disposed at a radial distance of generally 90° relative to longitudinal openings 610 and arranged parallel to longitudinal axis 204. Resilient arms 622 preferably include a forward extending portion 624, extending forwardly from rearward end 608, a connecting portion 626, arranged perpendicularly to forward extending portion 624, and a rearward facing portion 628, which extends rearwardly from connecting portion 626 and is arranged parallel to longitudinal axis 204. Rearward facing portion 628 terminates in a T-shape portion 630 on which is formed an extending protrusion 632.

Extending radially inwardly from rearward end 608 is a circumferential ring 634, which defines an inner forwardly facing surface 638 abutting inner surface 604 of syringe sleeve 600. Cylindrical wall 609 and circumferential ring 634 define a bore 636 extending longitudinally through syringe sleeve 600 and parallel to longitudinal axis 204.

One or more, preferably two diametrically opposite, rearward resilient arms 640 extend longitudinally rearwardly, arranged in the axial direction of longitudinal axis 204 and at a radial distance of generally 90° relative to forward resilient arms 622. Rearward resilient arms 640 extend rearwardly from a point adjacent circumferential ring 634. A radially inwardly extending protrusion 642 is formed at a rearward end of rearward resilient arm 640. Rearward resilient arms 640 include an outer surface 644, an inner surface 646 and a recess 648 formed on a rearward portion of outer surface 644.

One or more, preferably two, guide grooves 650 extend longitudinally and are arranged parallel to longitudinal axis 204. Guide grooves 650 extend along inner surface 604 from forward end 606 to the vicinity of rearward end 608.

Reference is now made to FIG. 8A, which is a simplified pictorial view illustration of plunger rod 800 forming part of AIDAHVM 100 of FIG. 1, and to FIGS. 8B-8D, which are, respectively, a simplified top view illustration, a simplified side view illustration and a simplified sectional view illustration of plunger rod 800 as shown in FIG. 8A.

As seen in FIGS. 8A-8D, plunger rod 800 is an integrally formed element, preferably formed of plastic and arranged along longitudinal axis 204. Plunger rod 800 includes an outer surface 802 and has a forward end 804 and a rearward end 806. Forward end 804 of plunger rod 800 includes a forwardly extending protrusion 808 formed thereon.

Extending rearwardly from rearward end 806 is a substantially hollow rear portion 810 defining a rearward edge 811. Extending rearwardly from substantially hollow rear portion 810 are one or more, typically two, extension tabs 812. A recess 814 is formed in substantially hollow rear portion 810.

One or more, typically two, longitudinal guide ribs 816 are formed on an outer surface of substantially hollow rear portion 810. Longitudinal guide ribs 816 extend parallel to axis 204 along substantially hollow rear portion 810. Substantially hollow rear portion 810 also includes one or more, typically two, protrusions 818 formed thereon, preferably disposed at a radial distance of generally 90° relative to longitudinal guide ribs 816. Preferably, protrusions 818 include a rearward facing inclined surface 820.

Figure 9A:
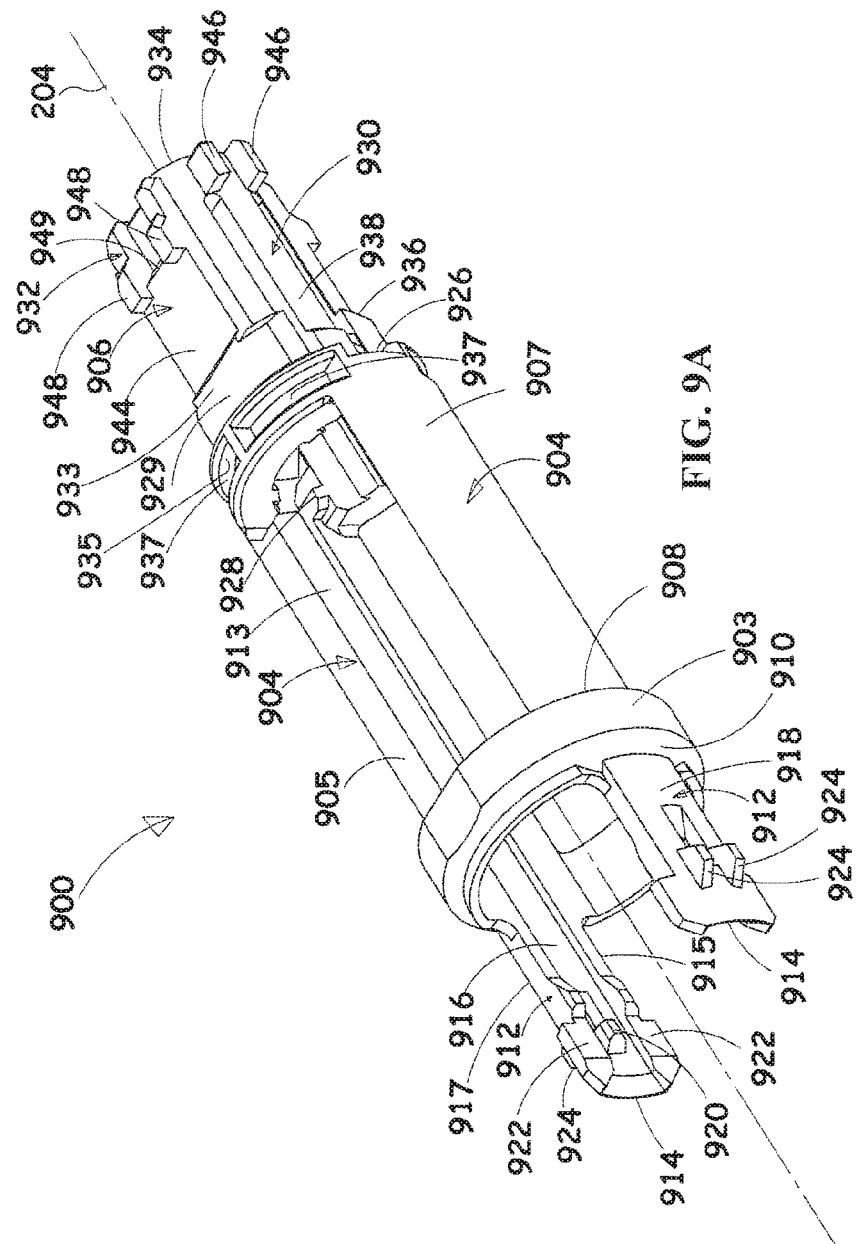
FIG. 9A is a simplified pictorial view illustration of a control unit forming part of the AIDAHVM of FIG. 1.

Reference is now made to FIG. 9A, which is a simplified pictorial view illustration of control unit 900 forming part of AIDAHVM 100 of FIG. 1, and to FIGS. 9B-9E, which are, respectively, a simplified side view illustration, a simplified top view illustration, and simplified sectional view illustrations of control unit 900 as shown in FIG. 9A.

As seen in FIGS. 9A-9E, control unit 900 is an integrally formed element, preferably formed of plastic and arranged along the longitudinal axis 204. Control unit 900 includes a forward circumferential ring 903, connected by one or more, preferably two, rearward extending arms 904 to a rearward body portion 906. Forward circumferential ring 903 defines a rearward ring end 908 and a forward ring end 910. Rearward extending arms 904 define an inner surface 905 and an outer surface 907.

One or more, typically two, forward resilient arms 912 extend forwardly from forward ring end 910 and are arranged parallel to longitudinal axis 204. Forward resilient arms 912 define a forward end 914, an inner surface 916 and an outer surface 918. A longitudinal groove 913 extends along the entire length of rearward extending arm 904 and continues along the entire length of forward resilient arm 912.

Disposed within longitudinal groove 913, in the vicinity of forward end 914, along an axis that is perpendicular to longitudinal axis 204, is a radially inwardly extending protrusion 920. Forward resilient arm 912 also defines two edges 915 and 917 on opposite side of longitudinal groove 913.

Edges 915 and 917 include lateral protrusions 922 adjacent forward end 914 and extending rearwardly therefrom.

Extending radially outwardly from outer surface 918 of each of forward resilient arms 912 is an external protrusion 924, disposed in vicinity of forward end 914.

Each of rearward extending arms 904 defines a rearward facing edge 926. Abutting rearward facing edges 926 are inwardly radially extending rearward protrusions 928.

Rearward body portion 906 of control unit 900 includes one or more, preferably two diametrically opposite, forward facing portions 929, one or more, preferably two diametrically opposite, intermediate portions 932 and a generally annular end portion 934. Preferably, generally annular end portion 934 includes two slightly elongate sections at locations diametrically opposite one another and is connected, at a forward end thereof along the elongate sections, to intermediate portions 932, which are in turn connected, at a forward end, to forward facing portions 929.

Forward facing portions 929 preferably include a rearward portion 933 and a forward portion 935, which preferably include a common inner wall section. One or more recesses 937 are formed in an outer wall of forward portion 935.

One or more, preferably two diametrically opposite, resilient arms 930 extend forwardly from generally annular end portion 934, preferably parallel to longitudinal axis 204 and forward resilient arms 912, at a radial distance of generally 90° relative to the elongate sections of generally annular end portion 934.

Resilient arm 930 defines an outer surface 938 and an inner surface 940. An inwardly radially extending protrusion 942 extends from inner surface 940 of resilient arm 930 near a forward end thereof. Forward of inwardly radially extending protrusion 942, resilient arm 930 terminates in an inclined surface 936.

An intermediate outer surface 944 is defined between forward facing portion 929 and intermediate portion 932 on two opposite sides of rearward body portion 906 that are orthogonal to the plane of connecting resilient arms 930. Preferably, extending radially outwardly from generally annular end portion 934 are one or more, preferably four, rearward protrusions 946. Preferably, a pair of rearward protrusions 946 are located on generally annular end portion 934 adjacent opposite lateral ends of each of resilient arms 930.

Preferably, extending radially outwardly from generally annular end portion 934 are also preferably formed a pair of spaced protrusions 948. Spaced protrusions 948 extend forwardly from generally annular end portion 934 to a rearward portion of intermediate outer surface 944 of intermediate portions 932. Generally annular end portion 934 and intermediate portion 932 form an inclined surface 949 therebetween. Preferably, spaced protrusions 948 are disposed at a radial distance of generally 90° relative to inwardly radially extending protrusions 942.

Each of forward facing portions 929 preferably defines a forward facing shoulder 950. Forward facing shoulders 950 are disposed slightly forwardly of inwardly radially extending protrusions 942, and disposed at a radial distance of generally 90° relative to inwardly radially extending protrusions 942.

Reference is now made to FIG. 10A, which is a simplified pictorial view illustration of rear housing 1000 forming part of AIDAHVM 100 of FIG. 1, and to FIGS. 10B-10D, which are, respectively, a simplified side view illustration, a simplified top view illustration and a simplified sectional view illustration of rear housing 1000 as shown in FIG. 10A.

As seen in FIGS. 10A-10D, rear housing 1000 is an integrally formed element, preferably formed of plastic and arranged along the longitudinal axis 204. Rear housing 1000 preferably includes an outer cylindrical portion 1002 and an inner cylindrical portion 1004 connected by a circumferential ring 1006. Inner cylindrical portion 1004 defines an outer surface 1008, an inner surface 1010 and a forward end 1012. Circumferential ring 1006 defines a forward facing annular edge surface 1014. The outer cylindrical portion 1002 defines an outer surface 1016 and a rearward end 1018.

Outer cylindrical portion 1002 rearwardly extends from forward facing annular edge surface 1014 to rearward end 1018. A circumferential ring 1020 is formed rearward of and adjacent to rearward end 1018.

One or more, preferably two diametrically opposite, radially outwardly extending protrusions 1022 are formed on outer surface 1016 of outer cylindrical portion 1002. Protrusions 1022 are preferably arranged perpendicular to longitudinal axis 204.

One or more, preferably two diametrically opposite, openings 1024 extend radially through outer cylindrical portion 1002, disposed at a radial distance of generally 90° relative to protrusions 1022.

Inner cylindrical portion 1004 is substantially hollow, open at forward end 1012 and partially closed at a rearward end by a circumferential flange 1026, defining an inner forwardly facing surface 1028, an outer rearwardly facing edge 1029, and an opening 1027 extending longitudinally rearwardly from the outer rearwardly facing edge 1029.

One or more, preferably two diametrically opposite, resilient arms 1030 are disposed in one or more, preferably two diametrically opposed, hollow portions of inner cylindrical portion 1004 rearward of forward facing annular edge surface 1014. Resilient arms 1030 extend forwardly from the circumferential flange 1026 of the inner cylindrical portion 1004.

Resilient arms 1030 include a T-shaped forward end 1032, defining two lateral extensions 1034 disposed therealong. One or more, preferably two, spaced radially outward protrusions 1038 are formed on an outer surface 1036 of resilient arms 1030 adjacent forward end 1032.

Reference is now made to FIG. 11A, which is a simplified pictorial view illustration of Resilient Dampening Element (RDE) 1100 forming part of AIDAHVM 100 of FIG. 1, and to FIGS. 11B-11C, which are, respectively, a simplified side view illustration and a simplified top view illustration of RDE 1100 as shown in FIG. 11A.

As seen in FIGS. 11A-11C, RDE 1100 is an integrally formed elongate element arranged along longitudinal axis 204. RDE 1100 is preferably formed of thermoplastic material, such as polyethylene, or any other suitable material that allows either plastic extension or elastic extension or both.

RDE 1100 preferably includes a forward holding portion 1102, an intermediate dampening portion 1104 and a rearward holding portion 1106, arranged longitudinally along longitudinal axis 204.

As seen in FIGS. 11A-11C, the cross-sectional area of intermediate dampening portion 1104 is substantially less than the cross-sectional area of both the forward holding portion 1102 and the rearward holding portion 1106.

Forward holding portion 1102 of RDE 1100 defines a forward end 1108, and rearward holding portion 1106 defines a rearward end 1110. Forward holding portion 1102 extends rearwardly from forward end 1108 to a rearward facing edge 1112 and rearward holding portion 1106 defines a forward facing edge 1114.

Rearward holding portion 1106 and forward holding portion 1102 are connected by intermediate dampening portion 1104, which is disposed longitudinally between rearward facing edge 1112 of the forward holding portion 1102 and the forward facing edge 1114 of the rearward holding portion 1106.

Forward holding portion 1102 includes a forward broadened section 1116 defining a rearward facing edge 1118, an intermediate section 1120, extending rearwardly therefrom, and an annular flange 1122, disposed rearwardly of intermediate section 1120. The cross-sectional area of intermediate section 1120 is less than the cross-sectional area of forward broadened section 1116. Forward broadened section 1116 and annular flange 1122 are typically of equal cross-sectional area and are spaced apart by intermediate section 1120.

Formed on forward facing edge 1114 is a forward extending projection 1124 arranged along longitudinal axis 204. Forward extending projection 1124 defines a forward facing edge 1126. One or more, preferably two diametrically opposite, protrusions 1128 are disposed on forward facing edge 1126. Protrusions 1128 preferably extend in a forward direction from forward facing edge 1126 and radially outwardly relative to axis 204.

Reference is now made to FIG. 12A, which is a simplified pictorial view illustration of trigger button 1200 forming part of AIDAHVM 100 of FIG. 1, and to FIGS. 12B-12E, which are, respectively, a simplified top view illustration, a simplified side view illustration and simplified sectional view illustrations of trigger button 1200 as shown in FIG. 12A.

As seen in FIGS. 12A-12E, trigger button 1200 is an integrally formed element, preferably formed of plastic and arranged along longitudinal axis 204.

Trigger button 1200 has a generally cylindrical configuration and defines an inner surface 1202, an outer surface 1204, an open forward end 1206 and a closed rearward end 1208.

Extending radially outward from outer surface 1204 are one or more circumferentially spaced projections 1210. Adjacent each of projections 1210, an elongate longitudinal recess 1211 is typically formed in outer surface 1204. Extending rearwardly from forward end 1206 are one or more, preferably two diametrically opposite, hollow generally rectangular recesses 1212.

One or more, preferably two, longitudinal resilient projections 1214 extend forwardly from closed rearward end 1208. Longitudinal resilient projections 1214 and generally rectangular recesses 1212 are aligned along a mutual axis that is preferably perpendicular to longitudinal axis 204.

Extending longitudinally forward from closed rearward end 1208 to forward end 1206 are one or more, preferably four circumferentially spaced, guide ribs 1216. Guide ribs 1216 are preferably arranged along axis 204 and parallel to the longitudinal resilient projections 1214.

Figure 13B:
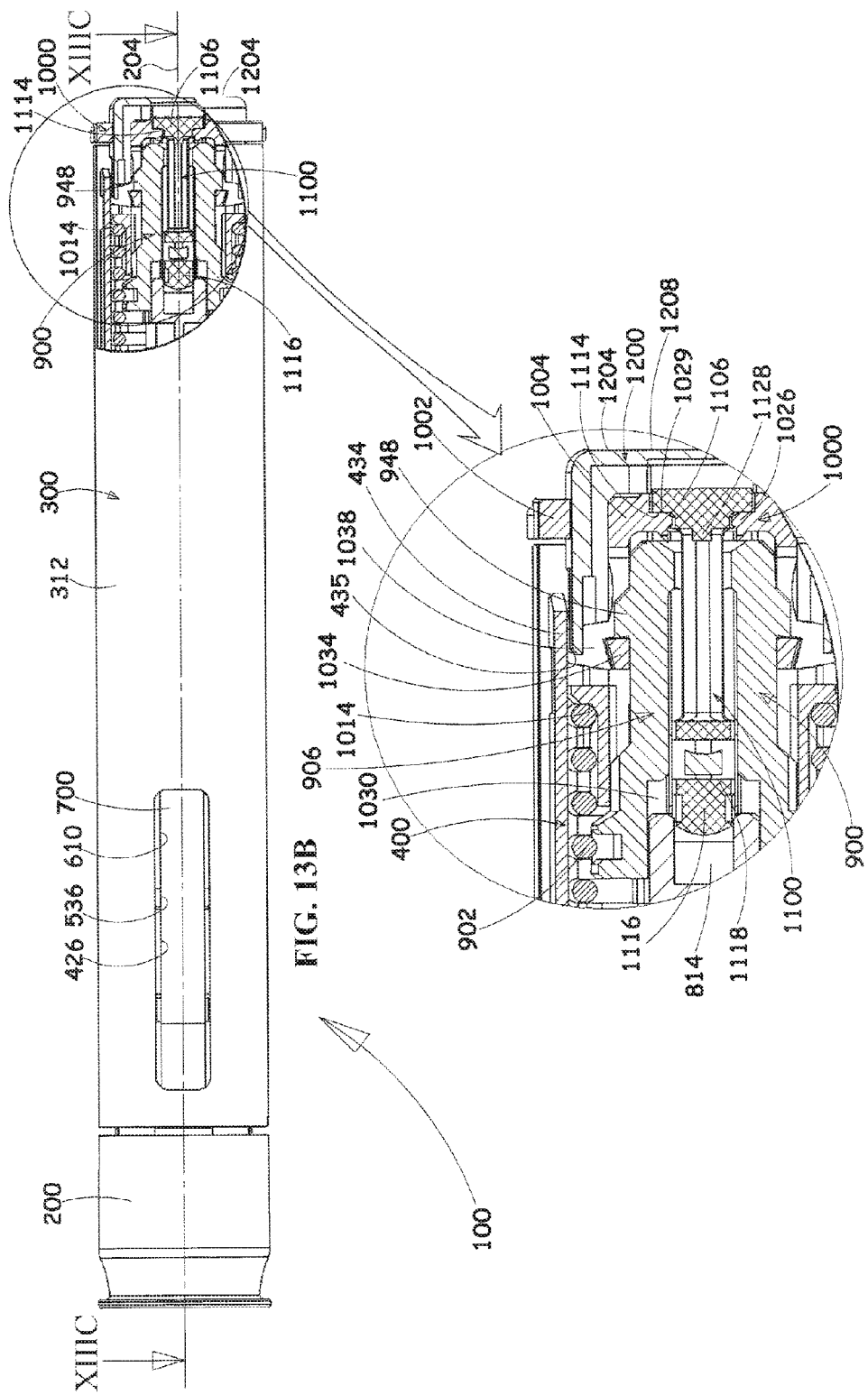
FIG. 13B is a simplified, partially cut away, top view illustration of the AIDAHVM as shown in FIG. 13A.
Figure 13C:
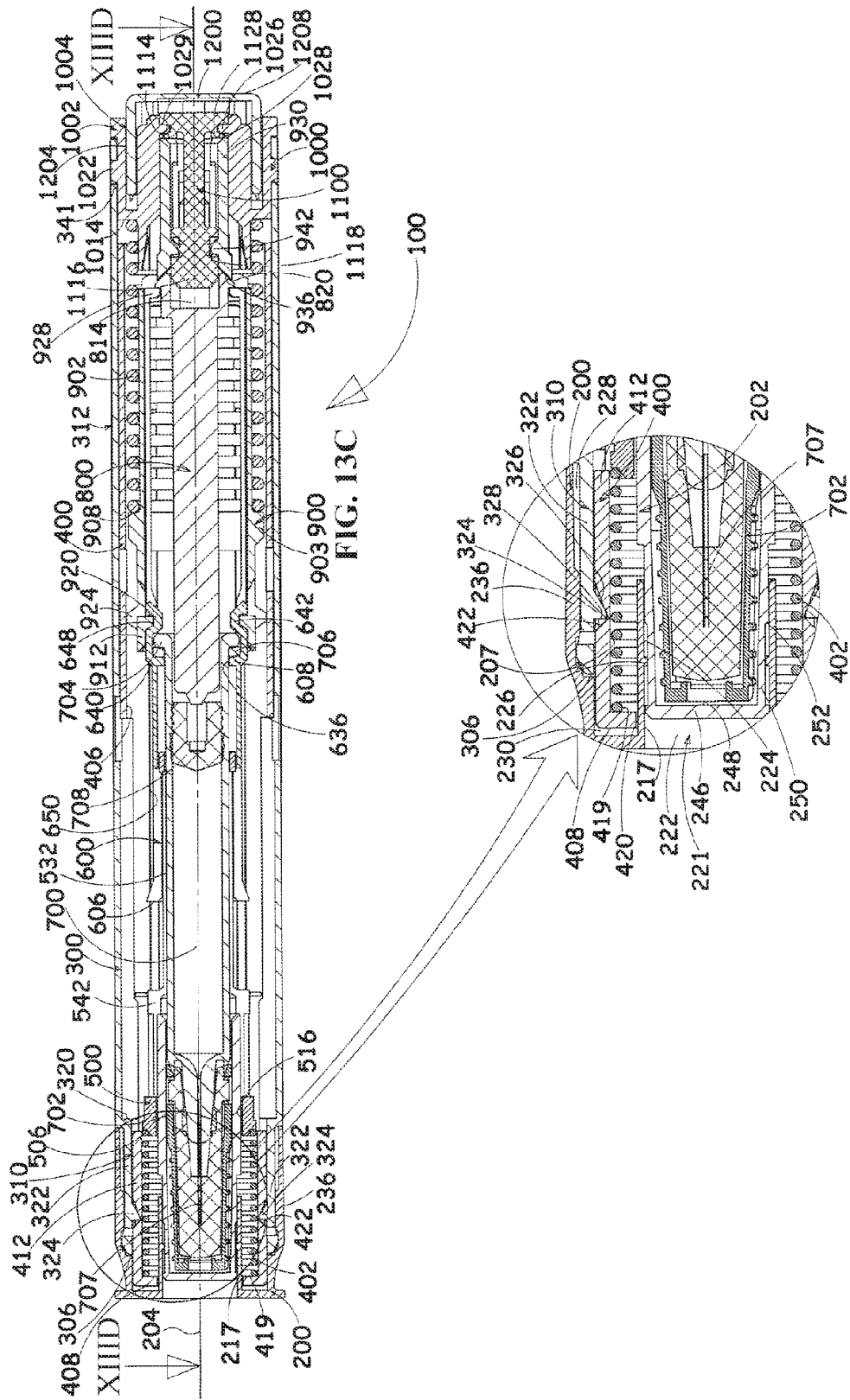
FIGS. 13C and 13D are simplified sectional view illustrations of the AIDAHVM as shown in FIG. 13A, taken along lines and XIIID-XIIID, in FIGS. 13B and 13C, respectively.
Figure 13D:
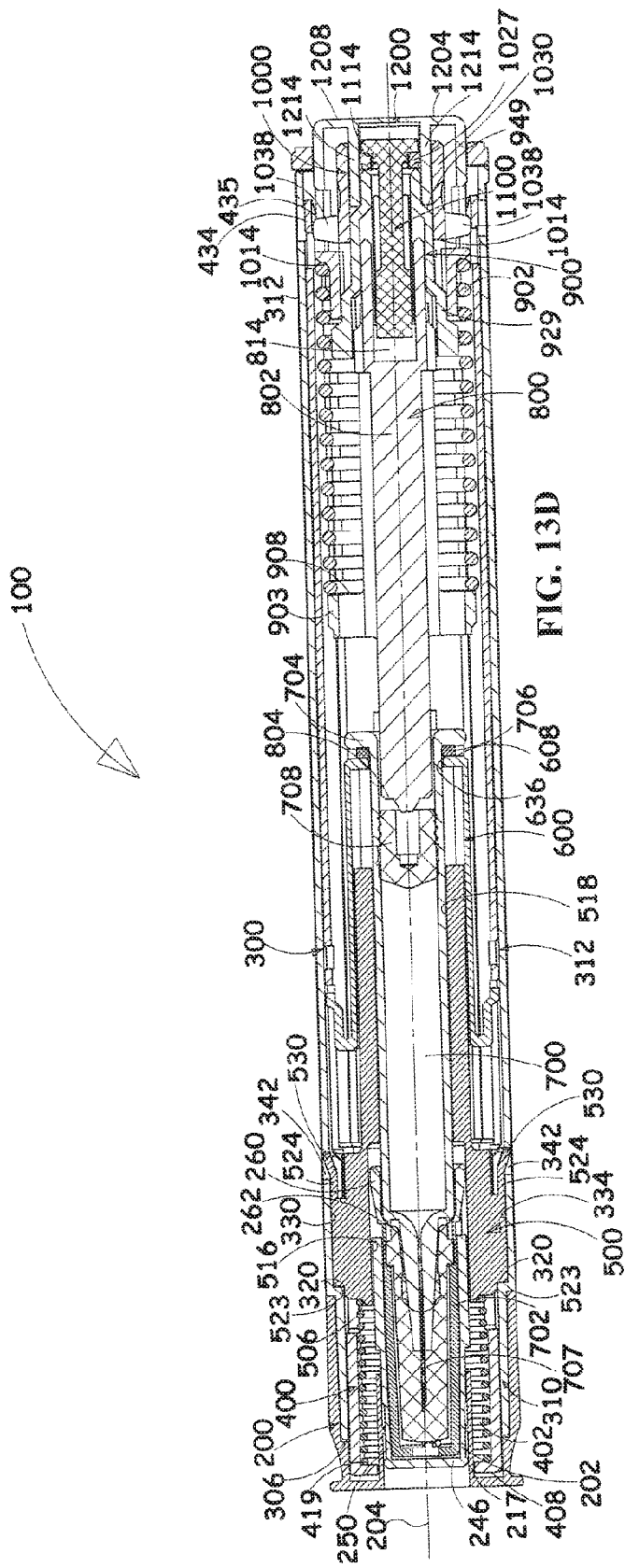

Reference is now made to FIG. 13A, which is a simplified pictorial view illustration of the AIDAHVM of FIG. 1 in a storage orientation, and to FIGS. 13B-13D, which are, respectively, a simplified top view illustration and simplified sectional view illustrations of the AIDAHVM as shown in FIG. 13A.

As seen in FIGS. 13A-13D, AIDAHVM 100 is in a locked storage orientation, in which relative axial movement between the components thereof is prevented, except as described hereinbelow. In the locked storage orientation shown in FIGS. 13A-13D, needle 707 of syringe 700 is covered by RNS 702.

As seen in FIGS. 13A-13D, fixed sleeve 500 is disposed within front housing 300 and is attached thereto by means of engagement of the forward longitudinal ribs 524 of the fixed sleeve 500 within elongate slots 330 of front housing 300. Forward longitudinal ribs 524 are inserted within the forward inner cavity portion 334 and are held within by the elongate elements 336. Radial extensions 530 of the forward longitudinal ribs 524 are fixedly held within the apertures 342 of the front housing 300 and limit rearward axial movement of the fixed sleeve 500 relative to the front housing 300. The forwardly facing edge 523 of the forward longitudinal ribs 524 of the fixed sleeve 500 abuts the forward end 320 of the relatively long rearward portion 312 of the front housing and thus prevents forward axial movement of the fixed sleeve 500 relative to the front housing 300.

In the storage orientation seen in FIGS. 13A-13D, spring 402 is compressed and fixedly held between forward end 506 of the fixed sleeve 500 at its rearward end and rearward facing edge 419 of needle shield 400 at its forward end. Axial forward movement of needle shield 400 relative to front housing 300 under the urging of spring 402 is prevented by the engagement of internally extending protrusion 324 of the resilient arms 322 of the front housing 300 with recessed portions 422 of needle shield 400. The engagement of internally extending protrusion 324 with recessed portions 422 is achieved by the inwardly tapered surface 326 and the forward facing edge 328 forming a stop with recessed portions 422 of needle shield 400. Resilient arms 322 of front housing 300 are supported at their outer surface by rectangular axial protrusions 236 of exterior RNS remover 200.

The engagement of the resilient arms 322 of the front housing 300 with the recessed portions 422 of the needle shield 400 in the storage orientation maintains the distance between the forward end 306 of the front housing 300 and the forward end 408 of the needle shield 400, and thereby the length of the AIDHVM 100, at a minimum. The distance between the forward end 306 of the front housing 300 and the forward end 408 of the needle shield 400, and thereby the length of the AIDHVM 100, is increased only following the removal of the exterior RNS remover 200 and the interior RNS remover 202, which disengages resilient arms 322 of front housing 300 from recessed portions 422 of needle shield 400, as described further hereinbelow with reference to FIGS. 14A-14C.

Interior portion 228 of exterior RNS remover 200 surrounds relatively short forward portion 310 of front housing 300 and forward cavity 230 of exterior RNS remover 200 partially surrounds the forward portion 412 of the needle shield 400. Cylindrical wall portion 217 is positioned within the opening 420 of needle shield 400. Interior RNS remover 202 is positioned partially within the forward cavity portion 222 and partially within the rearward cavity portion 224 of cylindrical cavity 221 of exterior RNS remover 200.

Annular rearward facing flange 226 of exterior RNS remover 200 is movably positioned along the length of the forward portion 250 between the first forwardly facing shoulder 252 and the circumferential ring 246 of the interior RNS remover 202. This relative arrangement between the annular rearward facing flange 226 of the exterior RNS remover 200 and the forward portion 250 of the interior RNS remover 202 allows limited axial relative movement between the interior RNS remover 202 and the exterior RNS remover 200, along the length defined between the circumferential ring 246 and the first forwardly facing shoulder 252, to compensate for tolerance inaccuracies of AIDHVM 100 and syringe 700 that may result from the manufacturing process.

Interior RNS remover 202 fixedly holds RNS 702 within. RNS 702 is held at a forward end by rearward facing inner wall 248. A rearward side of RNS 702 is snap-fit into inwardly radially extending arms 262 of connectors 260 of interior RNS remover 202. Additionally, interior RNS remover 202 is partially inserted into the forward inner bore 516 of the fixed sleeve 500.

Syringe 700 is located within bore 636 of syringe sleeve 600 and rearward inner bore 518 of fixed sleeve 500. Syringe 700 is fixedly held relative to syringe sleeve 600 by situating flange 704 of syringe 700 forward of radial protrusions 642 of rearward resilient arm 640 of syringe sleeve 600, between radial protrusions 642 and resilient ring 706, attached to rearward end 608 of syringe sleeve 600.

The longitudinal opening 610 of the syringe sleeve 600 and the longitudinal indication opening 536 of the fixed sleeve 500 are positioned to allow visual examination of the contents of syringe 700 through transparent portion of front housing 300. Needle 707 of the syringe 700 is fixedly attached to the syringe 700, preferably by use of an adhesive material.

Rearward longitudinal ribs 532 of the fixed sleeve 500 are inserted into guide grooves 650 of the syringe sleeve 600, to ensure proper alignment between the fixed sleeve 500 and the syringe sleeve 600. Engagement of ribs 532 and guide grooves 650 allows relative axial movement and prevents relative rotational movement between fixed sleeve 500 and syringe sleeve 600.

Relative axial movement between syringe sleeve 600 and control unit 900 is prevented by engagement of radially inwardly extending protrusions 920 of forward resilient arms 912 of control unit 900 with recesses 648 of rearward resilient arms 640 of syringe sleeve 600. External protrusions 924 of forward resilient arms 912 engage inner surface 406 of the needle shield 400 to prevent radially outward movement of forward resilient arms 912.

Spring 902 is compressed and fixedly held between rearward ring end 908 of the forward circumferential ring 903 of the control unit 900 at a forward end and by forward facing annular edge surface 1014 of the rear housing 1000 at a rearward end thereof. Axial forward movement of control unit 900, under urging of spring 902 is prevented by engagement of spaced protrusions 948 of intermediate portion 932 of rearward body portion 906 of control unit 900 with lateral extensions 1034 of the resilient arms 1030 of the rear housing 1000. Spaced radially outward protrusions 1038 of resilient arms 1030 engage inner surface 435 of needle shield 400 to prevent radially outward movement of resilient arms 1030.

Relative axial movement between rear housing 1000 and front housing 300 is prevented by insertion of protrusions 1022 of the outer cylindrical portion 1002 of the rear housing 1000 into rearward apertures 341 of front housing 300.

RDE 1100 is inserted into the opening 1027 of the rear housing 1000. Forward axial movement of RDE 1100 relative to rear housing 1000 is prevented by engagement of forward facing edge 1114 of RDE 1100 with outer rearwardly facing edge 1029 of circumferential flange 1026 of rear housing 1000. Rearward axial movement of RDE 1100 relative to rear housing 1000 is prevented by engagement of protrusions 1128 of RDE 1100 with inner forwardly facing surface 1028 of circumferential flange 1026 of the rear housing 1000.

Rearward facing edge 1118 of forward broadened section 1116 of RDE 1100 is disposed forwardly of inwardly radially extending protrusions 942 of connecting resilient arms 930 of control unit 900. Forward broadened section 1116 of RDE 1100 is located within recess 814 of plunger rod 800.

Inclined surfaces 936 of connecting resilient arms 930 of the control unit 900 are positioned against the rearward facing inclined surfaces 820 of the diametrically opposite protrusions 818 of the plunger rod 800. Forward axial movement of plunger rod 800 is prevented by inwardly radially extending rearward protrusions 928 of the control unit 900 and rearward axial movement of plunger rod 800 is prevented by engagement of rearward facing inclined surfaces 820 of plunger rod 800 with inclined surfaces 936 of resilient arms 930 of control unit 900.

As seen particularly in FIGS. 13C and 13D, in the storage orientation, forward end 804 of plunger rod 800 is inserted into syringe 700 and is rearwardly spaced from piston 708 of syringe 700.

Outer surface 1204 of trigger button 1200 is positioned between the outer cylindrical portion 1002 and the inner cylindrical portion 1004 of the rear housing 1000, while the circumferentially spaced projections 1210 of the trigger button 1200 are disposed within openings 1024 of the outer cylindrical portion 1002 of the rear housing 1000. Rearward axial movement of trigger button 1200 relative to rear housing 1000 is prevented by location of projections 1210 of trigger button 1200 within openings 1024 of rear housing 1000.

Longitudinal resilient projections 1214 of the trigger button 1200 are disposed between forward facing portions 929 of rearward body portion 906 of control unit 900 and between diametrically opposite resilient arms 1030 of rear housing 1000. Forward axial movement of trigger button 1200 relative to rear housing 1000 is prevented by the location of the forward end of longitudinal resilient projections 1214 abutting inclined surface 949 of intermediate portion 932 of control unit 900.

It is appreciated that, if enabled, pressing the closed rearward end 1208 of the trigger button 1200 forwardly would, as described further hereinbelow, force longitudinal resilient projections 1214 of trigger button 1200 to slide over inclined surface 949 of intermediate portion 932 of control unit 900 and bend radially outwardly and thereby push resilient arms 1030 of the rear housing 1000 radially outwardly relative to the spaced protrusions 948 of control unit 900. However, in the storage orientation seen in FIGS. 13A-13D, forward movement of trigger button 1200 is prevented by the location of inner surface 435 of needle shield 400 adjacent to and radially outwardly of spaced radially outward protrusions 1038 of the rear housing 1000 which prevents radially outward movement of spaced radially outward protrusions 1038 of the rear housing 1000.

Figure 14A:
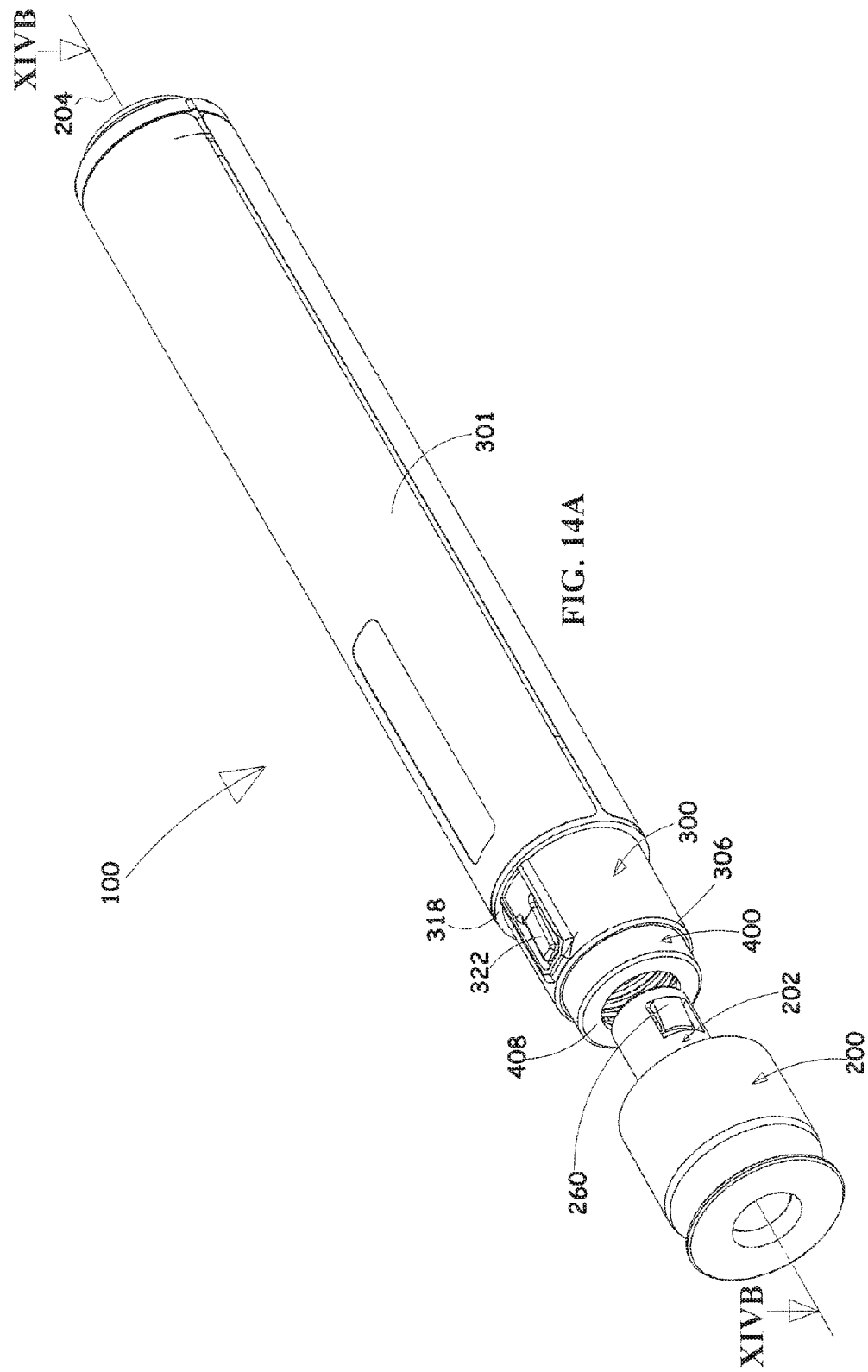
FIG. 14A is a simplified pictorial view illustration of the AIDAHVM of FIGS. 1-12D in a first operative orientation, following RNS removal.

Reference is now made to FIG. 14A, which is a simplified pictorial view illustration of AIDAHVM 100 in a first operative orientation following RNS removal and to FIGS. 14B-14C, which are simplified sectional view illustrations of the AIDAHVM as shown in FIG. 14A.

As seen in FIGS. 14A-14C, RNS 702 has been removed by forward axial displacement of exterior RNS remover 200 and interior RNS remover 202 relative to AIDAHVM 100, typically by a user pulling exterior RNS remover forwardly relative to front housing 300, thereby exposing needle shield 400 and needle 707.

In a first stage of the forward axial displacement of exterior RNS remover 200, exterior RNS remover 200 is forwardly axially displaceable relative to both front housing 300 and to interior RNS remover 202. The first stage continues until annular rearward facing flange 226 of exterior RNS remover 200 engages circumferential ring 246 of interior RNS remover 202.

In a second stage of the forward axial displacement of exterior RNS remover 200, exterior RNS remover 200 is forwardly axially displaceable relative to front housing 300 but is not forwardly axially displaceable relative to interior RNS remover 202. The second stage begins with the engagement of annular rearward facing flange 226 of exterior RNS remover 200 with circumferential ring 246 of interior RNS remover 202. During the second stage, exterior RNS remover 200 and interior RNS remover 202 are forwardly axially displaced together relative to front housing 300. During the second stage, engagement of RNS 702 by inwardly radially extending arms 262 of connectors 260 of interior RNS remover 202 also forwardly axially displaces RNS 702, thereby removing RNS 702 from syringe 700.

Following the removal of the exterior RNS remover 200, rectangular axial protrusions 236 of the exterior RNS remover 200 no longer support resilient arms 322 of the front housing 300. This allows for the inwardly tapered surface 326 of resilient arms 322 of front housing 300 are thereby free to slide over inclined surface of recessed portions 422 of needle shield 400 and thereby radially outwardly open, allowing forward movement of needle shield 400 under the urging of spring 402.

Under the urging of spring 402, needle shield 400 proceeds forwardly relative to front housing 300 until rearward edges 425 of longitudinal openings 424 of needle shield 400 engage extending protrusions 632 of forward resilient arms 622 of syringe sleeve 600.

As seen in FIGS. 14A-14C, in the first operative orientation, spaced radially outward protrusions 1038 of diametrically opposite resilient arms 1030 of rear housing 1000 are still radially supported by inner surface 435 of tabs 434 of needle shield 400.

Figure 15A:
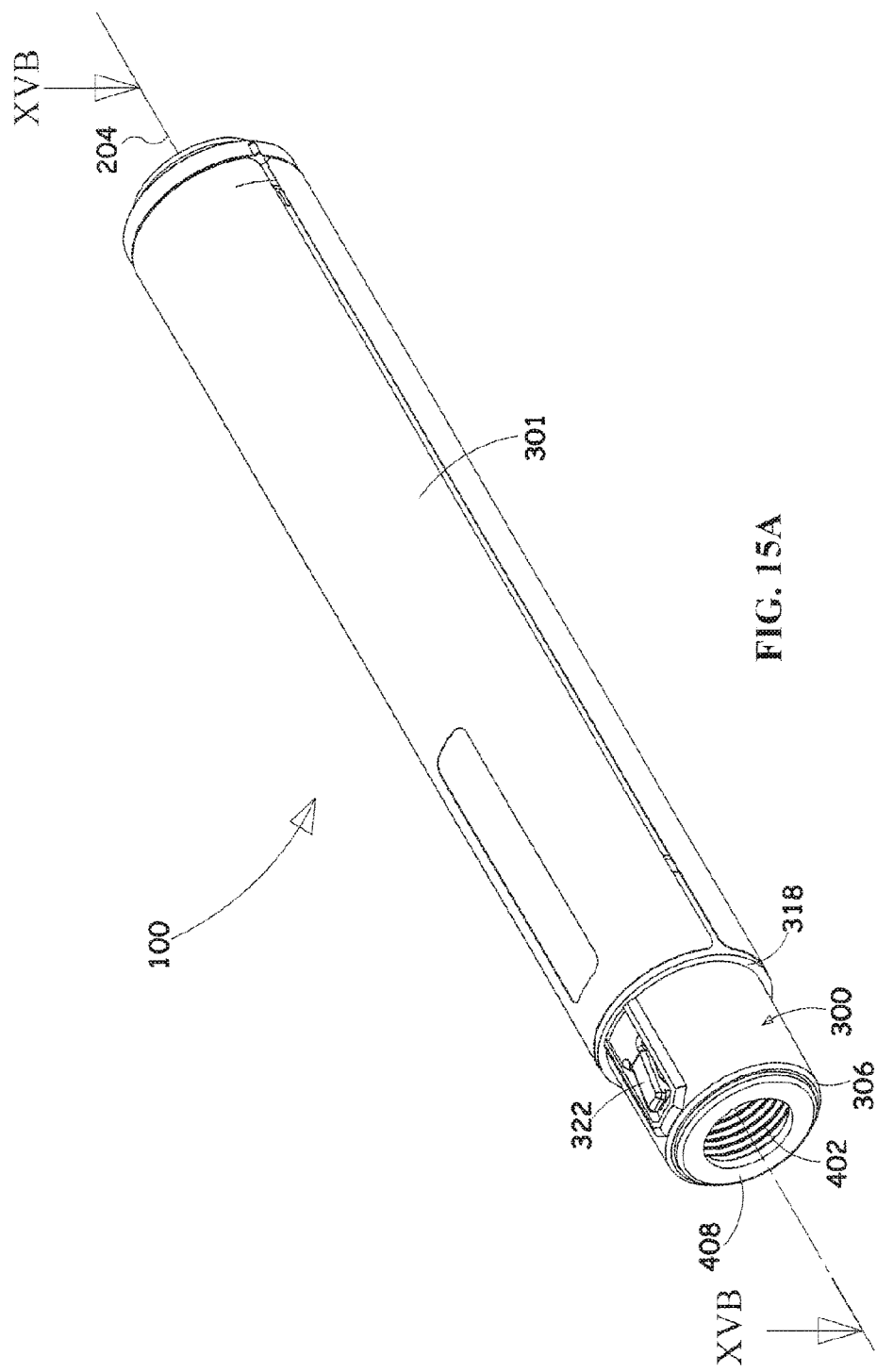
FIG. 15A is a simplified pictorial view illustration of the AIDAHVM of FIGS. 1-12D in a second operative orientation, pushing against an injection site.
Figures 15B, 15C:
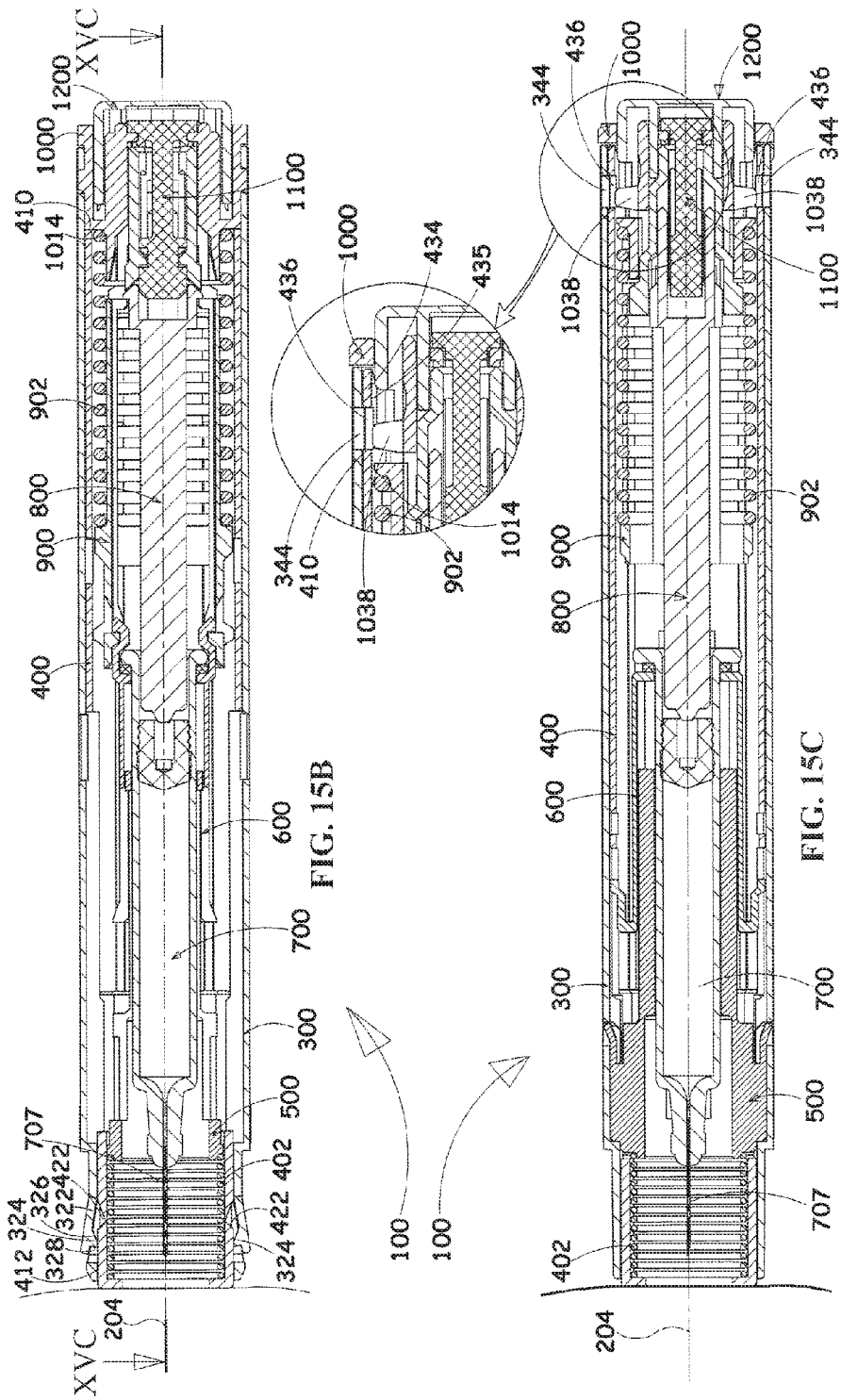
FIGS. 15B and 15C are simplified sectional view illustrations of the AIDAHVM as shown in FIG. 15A, taken along lines XVB-XVB and XVC-XVC, in FIGS. 15A and 15B, respectively.

Reference is now made to FIG. 15A, which is a simplified pictorial view illustration of AIDAHVM 100 in a second operative orientation, pushing against an injection site and to FIGS. 15B and 15C, which are simplified sectional view illustrations of AIDAHVM 100 as shown in FIG. 15A.

Following the removal of the RNS 702 from the AIDAHVM 100, needle shield 400 is axially rearwardly displaced relative to front housing 300, typically by the user pushing AIDAHVM 100 forwardly against an injection site. The axial rearward movement of needle shield 400 compresses spring 402 until rearward end 410 of needle shield 400 abuts forward facing annular edge surface 1014 of rear housing 1000. Axial rearward movement of needle shield 400 causes internally extending protrusions 324 of arms 322 of front housing 300 to slide into recessed portions 422 of the needle shield 400. Further axial rearward movement of needle shield relative to front housing 300 causes internally extending protrusions 324 of arms 322 to slide out of recessed portions 422 of needle shield 400 and to be pushed radially outwardly by outer surface of forward portion 412 of needle shield 400.

Following the rearward movement of the needle shield 400, the apertures 436 of the tabs 434 of the needle shield 400 are positioned in front of spaced radially outward protrusions 1038 of rear housing 1000 and in front of the rearward apertures 344 of front housing 300. In this orientation, spaced radially outward protrusions 1038 are no longer supported by inner surface 435 of tabs 434 of the needle shield 400.

Figure 16B:
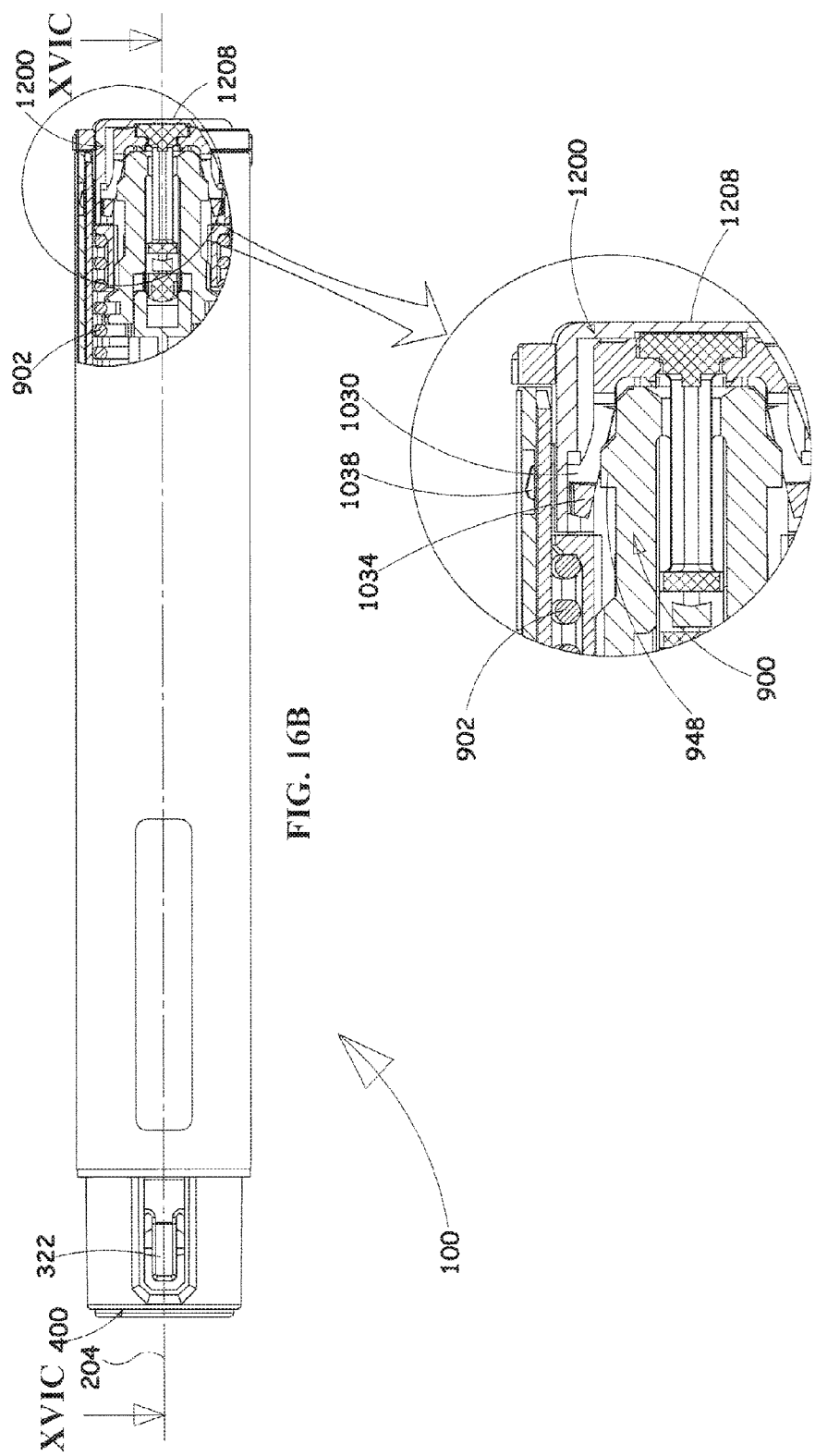
FIG. 16B is a simplified top view illustration of the AIDAHVM as shown in FIG. 16A.

Reference is now made to FIG. 16A, which is a simplified pictorial view illustration of AIDAHVM 100 in a third operative orientation, which is an activation orientation, and to FIGS. 16B-16D which are, respectively, a simplified top view illustration and simplified sectional view illustrations of AIDAHVM 100 as shown in FIG. 16A.

As seen in FIGS. 16A-16D, following rearward displacement of needle shield 400, AIDAHVM 100 is activated by forwardly displacing trigger button, typically by a user pushing closed rearward end 1208 of trigger button 1200. Forward displacement of trigger button 1200 causes longitudinal resilient projections 1214 of trigger button 1200 to slide over inclined surface 949 of control unit 900 and radially outwardly, thereby pushing resilient arms 1030 of rear housing 1000 radially outwardly. As described hereinabove with reference to FIGS. 15A-15C, spaced radially outward protrusions 1038 of resilient arms 1030 of rear housing 1000 are no longer supported by inner surface 435 of tabs 434 of needle shield 400, which frees trigger button 1200 to be moved axially forwardly. As described above, this allows longitudinal resilient projections 1214 of trigger button 1200 together with resilient arms 1030 of rear housing 1000 to bend radially outwardly. This forward movement also causes disengagement of lateral extensions 1034 of diametrically opposite resilient arms 1030 of rear housing 1000 from spaced protrusions 948 of intermediate portion 932 of control unit 900, thus freeing the control unit 900 to move axially forwardly under the urging of spring 902.

Figure 17A:
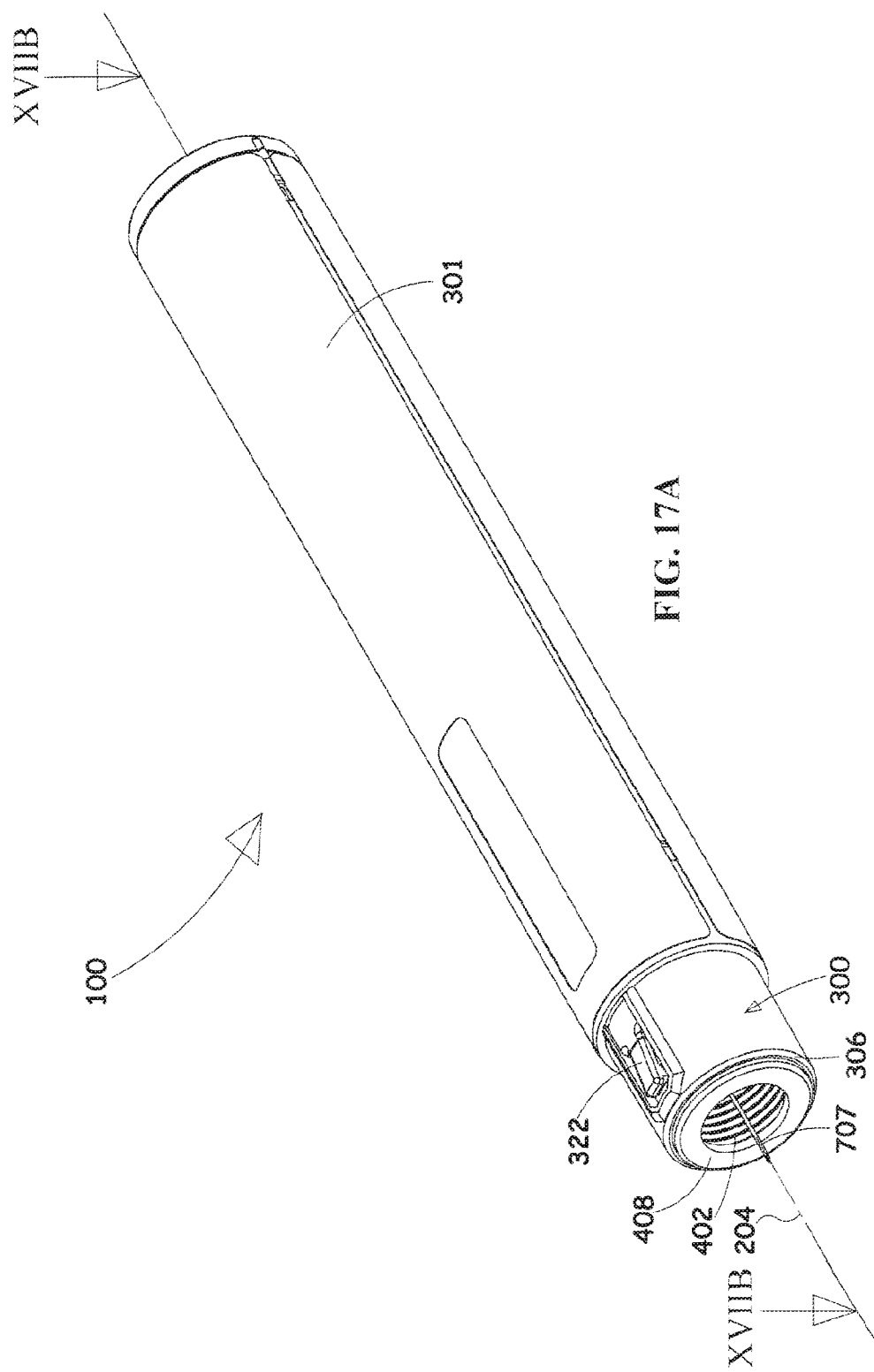
FIG. 17A is a simplified pictorial view illustration of the AIDAHVM of FIGS. 1-12D in a fourth operative orientation, including needle penetration, start of injection, injection and end of injection orientations.

Reference is now made to FIG. 17A, which is a simplified pictorial view illustration of AIDAHVM 100 in a fourth operative orientation, which includes needle penetration, start of injection, injection and end of injection orientations, to FIGS. 17B and 17C, which are simplified sectional view illustrations of AIDAHVM 100 as shown in FIG. 17A in a needle penetration operative orientation, FIGS. 18A and 18B, which are simplified sectional view illustrations of AIDAHVM 100 as shown in FIG. 17A in a start of injection operative orientation, FIGS. 19A-19C, which are, respectively, a simplified, partially cut away, front view illustration and simplified sectional view illustrations of AIDAHVM 100 as shown in FIG. 17A in an injection operative orientation, and to FIGS. 20A-20C, which are, respectively, a simplified, partially cut away, front view illustration and simplified sectional view illustrations of AIDAHVM 100 as shown in FIG. 17A in an end of injection operative orientation.

Referring now specifically to FIGS. 17A-17C, under the urging of spring 902, control unit 900 moves axially forwardly and forwardly displaces syringe sleeve 600 together with syringe 700. Needle 707 passes through opening 420 of needle shield 400 and penetrates the skin of the user, preferably achieving a desired penetration depth for administering the medication. Forward displacement of control unit 900 and syringe sleeve 600 under urging of spring 902 continues until inner forwardly facing surface 638 of syringe sleeve 600 abuts the rearward end 508 of the fixed sleeve 500. The forward displacement of control unit 900 positions external protrusions 924 of forward resilient arms 912 of control unit 900 within longitudinal indication openings 426 of needle shield 400 and forward apertures 340 of the front housing 300, thereby allowing forward resilient arms 912 of control unit 900 to bend radially outwardly.

Forward displacement of control unit 900 also causes inwardly radially extending protrusions 942 of resilient arms 930 of control unit 900 to forwardly displace rearward facing edge 1118 of forward broadened section 1116 of the RDE 1100 forwardly, thereby stretching RDE 1100.

Intermediate dampening portion 1104, which is the weakest portion of RDE 1100 is stretched at a force that is less than the axial force of spring 902. Intermediate dampening portion 1104 thereby absorbs a portion of the axial force of spring 902 during its elongation and provides for the dampening of the movement of control unit 900.

It is appreciated that in the orientation shown in FIGS. 17A-17C, plunger rod 800 is not yet in engagement with piston 708 of syringe 700.

Referring now specifically to FIGS. 18A-18B, under the further urging of spring 902, forward resilient arms 912 of the control unit 900 bend radially outwardly as control unit 900 is further displaced axially forwardly. The axial forward movement of control unit 900 causes radially inwardly extending protrusions 920 of forward resilient arms 912 to slide out of recesses 648 and forwardly along the outer surface 644 of rearward resilient arm 640 of syringe sleeve 600. The external protrusions 924 of the forward resilient arms 912 of the control unit 900 are positioned below of the indication openings 426 of the needle shield 400 and forward apertures 340 of front housing 300.

As seen in FIGS. 18A and 18B, further forward movement of the control unit 900 causes forward end 804 of plunger rod 800 to engage rearward end of piston 708 of syringe 700.

Upon engagement on the plunger rod 800 and piston 708, the hydraulic resistance of the medication within syringe 700 while flowing through needle 707 slows the forward axial movement of plunger rod 800 during further forward axial movement of control unit 900. Under the urging of the spring 902, the control unit 900 continues to move axially forward relative to plunger rod 800. Forward axial movement of control unit 900 relative to plunger rod 800 continues until rearward edge 811 of plunger rod 800 reaches forward facing shoulders 950 of rearward body portion 906 of control unit 900.

Forward axial movement of control unit 900 relative to plunger rod 800 causes forward broadened section 1116 of RDE 1100 to enter into recess 814 of substantially hollow rear portion 810 of plunger rod 800, thus preventing radial movement of forward broadened section 1116 of RDE 1100.

Forward axial movement of control unit 900 relative to plunger rod 800 also causes protrusions 818 of plunger rod 800 to push against inclined surfaces 936 of resilient arms 930, thus outwardly radially bending resilient arms 930 of control unit 900 and disengaging inwardly radially extending protrusions 942 of resilient arms 930 from rearward facing edge 1118 of RDE 1100, causing the application of the entire axial force of spring 902 to the forward movement of the plunger rod 800 against piston 708 of syringe 700. Thus, responsive to driving engagement of the at least one spring drive assembly, including spring 902, with control unit 900, plunger rod 800 and piston 708 the force limiting effect of at least one selectably operable spring energy output force limiter, RDE 1100, is automatically disabled.

Following further forward movement of control unit 900 under the continued urging of spring 902, longitudinal resilient projections 1214 of trigger button 1200 are no longer supported by inclined surface 949 of control unit 900 and bend radially inwardly to their original position together with resilient arms 1030 of rear housing 1000.

As seen in FIGS. 18A and 18B, spaced radially outward protrusions 1038 of resilient arms 1030 of rear housing 1000 are positioned neither within apertures 436 of tabs 434 of needle shield 400 nor within rearward apertures 344 of front housing 300.

The dampening of the axial force of spring 902 by means of RDE 1100 substantially decreases the axial force that is applied to syringe 700, and thereby reduces the probability of breakage of the syringe 700. The dampening also reduces the noise created at the end of the syringe 700 movement and at the engagement of the plunger rod 800 with piston 708 of the syringe 700.

The resilient ring 706 positioned on flange 704 of syringe 700 provides for even stress distribution over flange 704 of syringe 700, thus also reducing the probability of breakage of the syringe 700 and also decreasing the noise level.

It is appreciated that the axial force of the spring 902 and the cross-sectional area of RDE 1100 may be selected based on the medication being administered and the hydraulic force created thereby, thus providing a range of injector forces without compromising the forces applied during injection.

Referring now specifically to FIGS. 19A-19C, further forward axial movement of control unit 900, under urging of spring 902, produces forward axial movement of plunger rod 800 and piston 708 of syringe 700. Forward axial movement of control unit 900, plunger rod 800 and piston 708 continues as the medication in syringe 700 is injected forwardly into the injection site. As the forward movement continues lateral protrusions 922 of forward resilient arms 912 of control unit 900 bend radially outwardly above inclined edge 620 of the syringe sleeve 600 and further slide over protrusions 542 of forward cylindrical portion 510 of fixed sleeve 500.

Referring now specifically to FIGS. 20A-20C, following the completion of the injection piston 708 of syringe 700 is disposed at the forward end of syringe 700 and forward resilient arms 912 of the control unit 900 create an audible signal that indicates end of injection as lateral protrusions 922 of the forward resilient arms 912 of the control unit 900 disengage from protrusions 542 of forward cylindrical portion 510 of fixed sleeve 500.

Reference is now made to FIG. 21A, which is a simplified pictorial view illustration of AIDAHVM 100 in a discard orientation, and to FIGS. 21B-21C which are simplified sectional view illustrations of AIDAHVM 100 as shown in FIG. 21A.

Following the end of the injection of the medication in syringe 700, the user removes AIDAHVM 100 from the injection site. As the AIDAHVM 100 is removed, needle shield 400 moves axially forward relative to front housing 300 under the urging of spring 402 and covers needle 707 of syringe 700. The forward axial movement of needle shield 400 relative to front housing 300 continues until rearward edge 425 of longitudinal openings 424 of needle shield 400 engages extending protrusions 632 of forward resilient arms 622 of syringe sleeve 600.

As seen in FIGS. 21A-21C, internally extending protrusions 324 of resilient arms 322 of the front housing 300 slide into longitudinal indication opening 426 of the needle shield 400 adjacent its forward edge, as resilient arms 322 of front housing 300 returns to their original position.

In the discard orientation shown in FIGS. 21A-21C, needle 707 of syringe 700 is shielded by needle shield 400. Attempted retraction of needle shield 400 into front housing 300 by rearward axial displacement of needle shield 400 relative to front housing 300 is prevented, thereby preventing exposure of needle 707 of syringe 700, by location of forward edge of longitudinal indication opening 426 of needle shield 400 forward of forward facing edge 328 of the resilient arms 322 of the front housing 300.

It is appreciated that the term "at a radial distance of generally 90°" as used throughout the description of the present invention refers to a radial distance of 90°±5°.

It will be appreciated by persons skilled in the art that the present invention is not limited by what has been particularly shown and described hereinabove.

Rather the scope of the present invention includes both combinations and sub-combinations of various features described hereinabove as well as variations and modifications thereof which are not in the prior art.

The invention claimed is:

1. An automatic injection device configured for injection of a material stored in a syringe into an injection site, said syringe including a generally cylindrical storage container and a piston disposed within said generally cylindrical storage container, wherein axial forward displacement of said piston in said generally cylindrical storage container forces said material forwardly out of said generally cylindrical storage container, said automatic injection device comprising:

at least one spring drive assembly operative, when actuated:

to initially apply a first axial force to said syringe, thereby to axially displace said syringe in a forward direction; and thereafter, responsive to driving engagement with said piston, to apply a second axial force, greater than said first axial force, to said piston, thereby to axially displace said piston relative to said syringe in said forward direction, wherein the spring drive assembly is operative to engage said piston prior to application of said second axial force.

2. An automatic injection device according to claim 1 and wherein said at least one spring drive assembly comprises:
at least one spring; and
at least one selectably operable spring energy output force limiter,
said at least one selectably operable spring energy output force limiter being automatically disabled responsive to driving engagement of said at least one spring drive assembly with said piston,
said at least one spring providing said first axial force when said at least one selectably operable spring energy output force limiter is not disabled, and providing said second axial force when said at least one selectably operable spring energy output force limiter is disabled.

3. An automatic injection device according to claim 2 and wherein said at least one spring drive assembly stretches said at least one selectably operable spring energy output force limiter.

4. An automatic injection device according to claim 1 and wherein said syringe comprises a needle shield and said automatic injection device also comprises a needle shield remover, said needle shield remover including:
an exterior needle shield remover; and
an interior needle shield remover,
said exterior needle shield remover and said interior needle shield remover being configured to permit limited relative axial movement therebetween, thereby to compensate for manufacturing tolerance inaccuracies of said automatic injection device and said syringe.

5. An automatic injection device according to claim 4 and wherein said exterior needle shield remover and said interior needle shield remover are configured to be axially displaceable relative to each other at a first operative stage and not axially displaceable relative to each other at a second operative stage.

6. An automatic injection device according to claim 1 and also comprising a syringe sleeve and a relative movement restrictor operative to prevent relative movement of said syringe and said syringe sleeve when said automatic injection device is in a storage orientation.

7. An automatic injection device according to claim 6 and wherein said automatic injection device and said syringe sleeve are configured to allow visual examination of the contents of said syringe.

8. An automatic injection device according to claim 1 and also comprising a trigger button and a trigger button locking assembly operative to prevent forward movement of said trigger button when said automatic injection device is in a storage orientation.

9. An automatic injection device according to claim 1 and wherein said syringe also comprises a needle and a needle shield configured to prevent exposure of said needle in a post-injection orientation.

10. An automatic injection device according to claim 1 and also comprising:
a front housing;
a needle shield; and
a trigger button,
said automatic injection device being configured to be activatable by forwardly displacing said trigger button after rearwardly displacing said needle shield relative to said front housing.

11. An automatic injection device according to claim 10 and wherein said automatic injection device is configured such that forward displacement of said trigger button actuates said at least one spring drive assembly.

12. An automatic injection device according to claim 1 and also comprising a resilient ring positioned on said syringe.

13. An automatic injection device configured for injection of a material stored in a syringe into an injection site, said syringe including a generally cylindrical storage container and a piston disposed within said generally cylindrical storage container, wherein axial forward displacement of said piston in said generally cylindrical storage container forces said material forwardly out of said generally cylindrical storage container, said automatic injection device comprising:
at least one spring drive assembly operative, when actuated:
to initially apply a first axial force to a plunger to axially displace said plunger in a forward direction; and
thereafter, responsive to engagement of said plunger with said piston, to apply a second axial force, greater than said first axial force, to said piston, thereby to axially displace said piston relative to said syringe in said forward direction,
wherein the spring drive assembly is operative to engage said piston prior to application of said second axial force.

14. An automatic injection device according to claim 13 and wherein said plunger is spaced from said piston when said automatic injection device is in a storage orientation.

15. An automatic injection device according to claim 13 and wherein said at least one spring drive assembly is configured to forwardly displace said plunger into engagement with said piston.

16. An automatic injection device according to claim 13 and wherein said at least one spring drive assembly comprises:
at least one spring; and
at least one selectably operable spring energy output force limiter,
said at least one selectably operable spring energy output force limiter being automatically disabled responsive to driving engagement of said at least one spring drive assembly with said piston,
said at least one spring providing said first axial force when said at least one selectably operable spring energy output force limiter is not disabled, and providing said second axial force when said at least one selectably operable spring energy output force limiter is disabled.

17. An automatic injection device according to claim 13 and wherein said syringe comprises a needle shield and said automatic injection device also comprises a needle shield remover, said needle shield remover including:
an exterior needle shield remover; and
an interior needle shield remover,
said exterior needle shield remover and said interior needle shield remover being configured to permit limited relative axial movement therebetween, thereby to compensate for manufacturing tolerance inaccuracies of said automatic injection device and said syringe.

18. An automatic injection device configured for injection of a material stored in a syringe into an injection site, said syringe including a generally cylindrical storage container and a piston disposed within said generally cylindrical storage container, wherein axial forward displacement of said piston in said generally cylindrical storage container forces said material forwardly out of said generally cylindrical storage container, said automatic injection device comprising:

at least one spring drive assembly including:

at least one spring; and at least one selectably operable spring energy output force limiter, operative prior to axial forward displacement of said piston, said at least one selectably operable spring energy output force limiter being automatically disabled responsive to driving engagement of said at least one spring drive assembly with said piston, wherein said spring energy output force limiter is operative to engage said piston prior to said automatic disablement.

19. An automatic injection device according to claim 18 and wherein said at least one spring drive assembly stretches said at least one selectably operable spring energy output force limiter.

20. An automatic injection device according to claim 18 and wherein said at least one selectably operable spring energy output force limiter absorbs a portion of the force of said at least one spring drive assembly.

\* \* \* \* \*